(12) United States Patent
Hall et al.

(10) Patent No.: US 12,246,979 B2
(45) Date of Patent: *Mar. 11, 2025

(54) METHOD AND SYSTEM FOR PROVIDING ULTRAPURE WATER WITH FLEXIBLE LAMP CONFIGURATION

(71) Applicant: Evoqua Water Technologies LLC, Pittsburgh, PA (US)

(72) Inventors: Christopher Hall, Colorado Springs, CO (US); Bruce Lee Coulter, Rockford, IL (US)

(73) Assignee: Evoqua Water Technologies LLC, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/205,689

(22) Filed: Jun. 5, 2023

(65) Prior Publication Data

US 2023/0312386 A1    Oct. 5, 2023

Related U.S. Application Data

(60) Continuation of application No. 17/199,092, filed on Mar. 11, 2021, now Pat. No. 11,697,607, which is a
(Continued)

(51) Int. Cl.
*C02F 9/00* (2023.01)
*C02F 1/32* (2023.01)
(Continued)

(52) U.S. Cl.
CPC .............. *C02F 9/00* (2013.01); *C02F 1/325* (2013.01); *C02F 1/004* (2013.01); *C02F 1/008* (2013.01);
(Continued)

(58) Field of Classification Search
CPC .. C02F 1/004; C02F 1/008; C02F 1/04; C02F 1/20; C02F 1/325; C02F 1/42;
(Continued)

(56) References Cited

U.S. PATENT DOCUMENTS

| 4,430,226 A | 2/1984 | Hegde et al. |
| 6,137,240 A | 10/2000 | Bogdan |

(Continued)

FOREIGN PATENT DOCUMENTS

| CA | 2506039 C | 11/2005 |
| CN | 103827040 A | 5/2014 |

(Continued)

OTHER PUBLICATIONS

International Search Report for corresponding PCT/US2016/030708, dated Aug. 8, 2016.

(Continued)

*Primary Examiner* — Dirk R Bass

(57) ABSTRACT

A method and system of providing ultrapure water for semiconductor fabrication operations is provided. The water is treated by utilizing a free radical scavenging system. The free radical scavenging system can utilize actinic radiation with a free radical precursor compound, such as ammonium persulfate. The ultrapure water may be further treated by utilizing ion exchange media and degasification apparatus. A control system can be utilized to regulate a continuously variable intensity of the actinic radiation.

18 Claims, 12 Drawing Sheets

Related U.S. Application Data division of application No. 15/571,266, filed as application No. PCT/US2016/030708 on May 4, 2016, now Pat. No. 10,961,143.

(60) Provisional application No. 62/160,128, filed on May 12, 2015, provisional application No. 62/156,487, filed on May 4, 2015.

(51) Int. Cl.

| | |
|---|---|
| *C02F 1/00* | (2023.01) |
| *C02F 1/04* | (2023.01) |
| *C02F 1/20* | (2023.01) |
| *C02F 1/42* | (2023.01) |
| *C02F 1/44* | (2023.01) |
| *C02F 1/469* | (2023.01) |
| *C02F 1/70* | (2023.01) |
| *C02F 1/72* | (2023.01) |
| *C02F 103/04* | (2006.01) |
| *C02F 103/34* | (2006.01) |

(52) U.S. Cl.
CPC .............. *C02F 1/04* (2013.01); *C02F 1/20* (2013.01); *C02F 1/42* (2013.01); *C02F 2001/427* (2013.01); *C02F 1/441* (2013.01); *C02F 1/444* (2013.01); *C02F 1/4693* (2013.01); *C02F 1/4695* (2013.01); *C02F 1/70* (2013.01); *C02F 1/722* (2013.01); *C02F 2103/04* (2013.01); *C02F 2103/346* (2013.01); *C02F 2201/3227* (2013.01); *C02F 2201/326* (2013.01); *C02F 2209/20* (2013.01); *C02F 2301/08* (2013.01); *C02F 2303/18* (2013.01); *C02F 2305/023* (2013.01)

(58) Field of Classification Search
CPC ........ C02F 1/441; C02F 1/444; C02F 1/4693; C02F 1/4695; C02F 1/70; C02F 1/722; C02F 2001/427; C02F 2103/04; C02F 2103/346; C02F 2201/3227; C02F 2201/326; C02F 2209/20; C02F 2301/08; C02F 2303/18

See application file for complete search history.

(56) References Cited

U.S. PATENT DOCUMENTS

| | | |
|---|---|---|
| 6,997,578 B2 | 2/2006 | Culbert et al. |
| 2003/0155873 A1 | 8/2003 | O'Meara |
| 2005/0258763 A1 | 11/2005 | Sauska et al. |
| 2007/0205382 A1 | 9/2007 | Gaska et al. |
| 2010/0314551 A1 | 12/2010 | Bettles et al. |
| 2011/0210077 A1 | 9/2011 | Coulter |
| 2011/0210267 A1 | 9/2011 | Coulter |
| 2012/0261349 A1 | 10/2012 | Kolstad et al. |

FOREIGN PATENT DOCUMENTS

| | | |
|---|---|---|
| EP | 589926 B1 | 5/1996 |
| JP | H06198279 A | 7/1994 |
| JP | 2012038620 A | 2/2012 |
| JP | 2014508033 A | 4/2014 |
| JP | 2002263643 | 9/2022 |
| WO | 1998048447 A1 | 10/1998 |
| WO | 2008038548 A1 | 4/2008 |
| WO | 2012/099817 A2 | 7/2012 |

OTHER PUBLICATIONS

Chatellier, Xavier, "Communication Pursuant to Article 94(3) EPC," European Patent Application No. 16789987.1, mailed Jun. 17, 2019, 2 pages.

Tominaga, M., "Notification of Reasons for Refusal," Japanese Patent Application No. 2017-548940, mailed Jul. 7, 2020, 2 pages.

Unknown, "First Office Action", Chinese Patent Application No. 201680025700.3, mailed Apr. 1, 2020, 77 pages.

Third Office Action, corresponding Chinese Patent Application No. 201680025700.3, dated May 7, 2021.

Sharma, Hatinder, "Examination Report No. 1 for Standard Patent Application ," Australian Patent Application No. 2016257925, mailed Nov. 30, 2021, 4 pages.

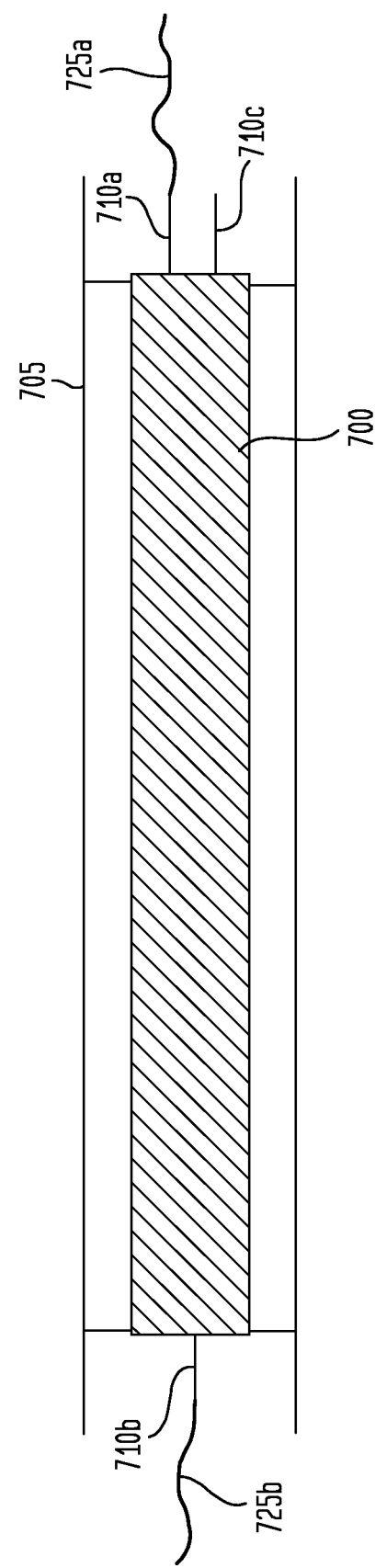

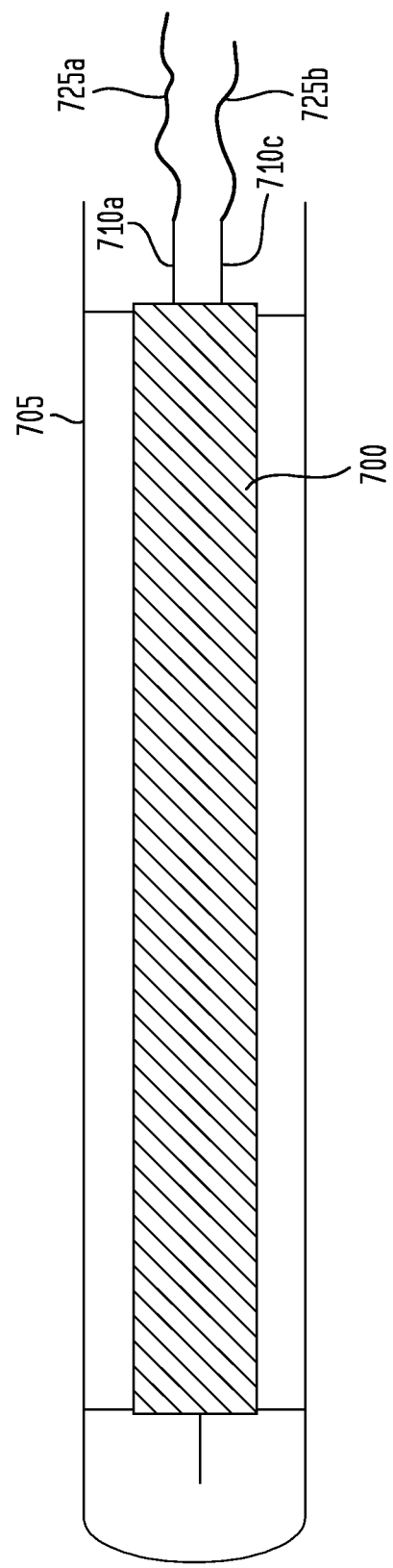

METHOD AND SYSTEM FOR PROVIDING ULTRAPURE WATER WITH FLEXIBLE LAMP CONFIGURATION

CROSS-REFERENCE TO RELATED APPLICATIONS

This application claims priority under 35 U.S.C. § 119(e) to U.S. Provisional Application No. 62/156,487, filed May 4, 2105, titled "FLEXIBLE ELECTRICAL LAMP CONFIGURATION FOR AN ADVANCED OXIDATION PROCESS" and to U.S. Provisional Application No. 62/160,128, filed May 12, 2105, titled "VARIABLE INTENSITY LAMP FOR AN ADVANCED OXIDATION PROCESS," each of which being incorporated herein by reference in its entirety for all purposes.

BACKGROUND

Aspects and embodiments disclosed herein relate to systems and methods of providing ultrapure water and, in particular, to systems and methods of reducing or maintaining a contaminant level of ultrapure water that can be used during fabrication of semiconductor devices or components thereof.

SUMMARY

One or more aspects relate to a system for treating water. The system comprises a primary actinic radiation reactor, a source of a persulfate precursor compound disposed to introduce at least one persulfate precursor compound into the primary actinic radiation reactor, a total organic carbon (TOC) concentration sensor located upstream of the primary actinic radiation reactor, a persulfate concentration sensor located downstream of the primary actinic radiation reactor, and a controller operatively coupled to receive at least one input signal from at least one of the TOC concentration sensor and the persulfate concentration sensor, and to generate a control signal that regulates a continuously variable intensity of the actinic radiation in the primary actinic radiation reactor based at least in part on the at least one input signal.

In some embodiments, the system further comprises a reverse osmosis unit located upstream of the primary actinic radiation reactor.

In some embodiments, the system further comprises a secondary actinic radiation reactor located downstream of the primary actinic radiation reactor.

In some embodiments, the system further comprises a particulate filter located downstream of the primary actinic radiation reactor.

In some embodiments, the system further comprises an ultrafiltration apparatus located downstream of from the primary actinic radiation reactor.

In some embodiments, the system further comprises at least one unit operation selected from the group consisting of a heat exchanger, a degasifier, a particulate filter, an ion purification apparatus, and an ion-exchange column.

In some embodiments, the ion-exchange column is located upstream of the TOC concentration sensor.

In some embodiments, the system further comprises a source of water located upstream of the primary actinic radiation reactor comprising one or more unit operations selected from the group consisting of a reverse osmosis filter, an electrodialysis device, an electrodeionization device, a distillation apparatus, an ion-exchange column, and combinations thereof.

In some embodiments, water from the source of water comprises less than about 25 ppb TOC.

In some embodiments, the system further comprises a TOC concentration sensor located downstream of the primary actinic radiation reactor.

In some embodiments, the reducing agent is sulfur dioxide.

In some embodiments, the controller is further operable to generate a control signal that regulates a rate at which the persulfate precursor compound is introduced into the primary actinic radiation reactor.

In some embodiments, the primary actinic radiation reactor includes an ultraviolet lamp with a double sided electrical connection.

In some embodiments, the ultraviolet lamp with the double sided electrical connection includes a first electrical connection to a first electrode on a first end of the lamp, a second electrical connection to a second electrode on the first end of the lamp, and a third electrical connection to the second electrode on a second end of the lamp.

In some embodiments, the system further comprises a source of a reducing agent disposed to introduce at least one reducing agent downstream from the primary actinic radiation reactor, and a reducing agent concentration sensor located downstream of a point of addition of the at least one reducing agent. The controller may be further configured to receive an input signal from the reducing agent concentration sensor and generate a control signal that regulates a continuously variable intensity of the actinic radiation in the primary actinic radiation reactor based at least in part on the input signal from the reducing agent concentration sensor.

In some embodiments, the controller is further operable to generate a control signal that regulates a rate at which the reducing agent is introduced to the system In accordance with another aspect, there is provided a method of treating water. The method comprises providing a water to be treated, measuring a total organic carbon (TOC) value of the water to be treated, introducing persulfate anions to the water to be treated based in part on at least one input signal of the measured TOC value of the water to be treated, introducing the water containing persulfate anions to a primary reactor, exposing the persulfate anions in the water to ultraviolet light in the reactor to produce an irradiated water stream, and adjusting a continuously variable intensity of the ultraviolet light based in part on at least one of an input signal selected from the group consisting of a TOC value of the water to be treated, a persulfate value of the water downstream of the reactor, and a rate of addition of persulfate anions.

In some embodiments, the method further comprises exposing the irradiated water to ultraviolet light in a secondary reactor located downstream of the primary reactor.

In some embodiments, the method further comprises removing dissolved solids and dissolved gases from the water.

In some embodiments, the method further comprises treating the water to be treated prior to providing the water to be treated to the reactor vessel.

In some embodiments, the method further comprises introducing a reducing agent to the irradiated water.

In some embodiments, the method further comprises measuring a reducing agent concentration value of the irradiated water.

In some embodiments, the method further comprises the reducing agent to the irradiated water based on the measured reducing agent concentration value.

In some embodiments, the reducing agent is sulfur dioxide.

In some embodiments, providing the water to be treated includes providing inlet water having a TOC value of less than about 25 ppb and treating the water includes reducing the TOC value of the water to less than 1 ppb.

In accordance with another aspect, there is provided a method of providing ultrapure water to a semiconductor fabrication unit. The method comprises providing inlet water having a TOC value of less than about 25 ppb, introducing at least one free radical precursor compound into the water, converting the at least one free radical precursor compound into at least one free radical scavenging species by exposing the at least one free radical precursor to a UV radiation from a source of UV radiation having a continuously variable UV radiation power output, removing at least a portion of any particulates from the water to produce the ultrapure water, and delivering at least a portion of the ultrapure water to the semiconductor fabrication unit.

In some embodiments, the method further comprises regulating a rate of addition of the at least one precursor compound based at least partially on the TOC value of the inlet water.

In some embodiments, the method further comprises regulating the UV radiation power output based at least partially on the TOC value of the inlet water.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing.

In the drawings:

FIG. 9B illustrates another embodiment of a double sided electrical connection lamp utilized in embodiments of a system in accordance with one or more embodiments;

FIG. 9C illustrates another embodiment of a double sided electrical connection lamp utilized in embodiments of a system in accordance with one or more embodiments.

DETAILED DESCRIPTION

Figure 1:
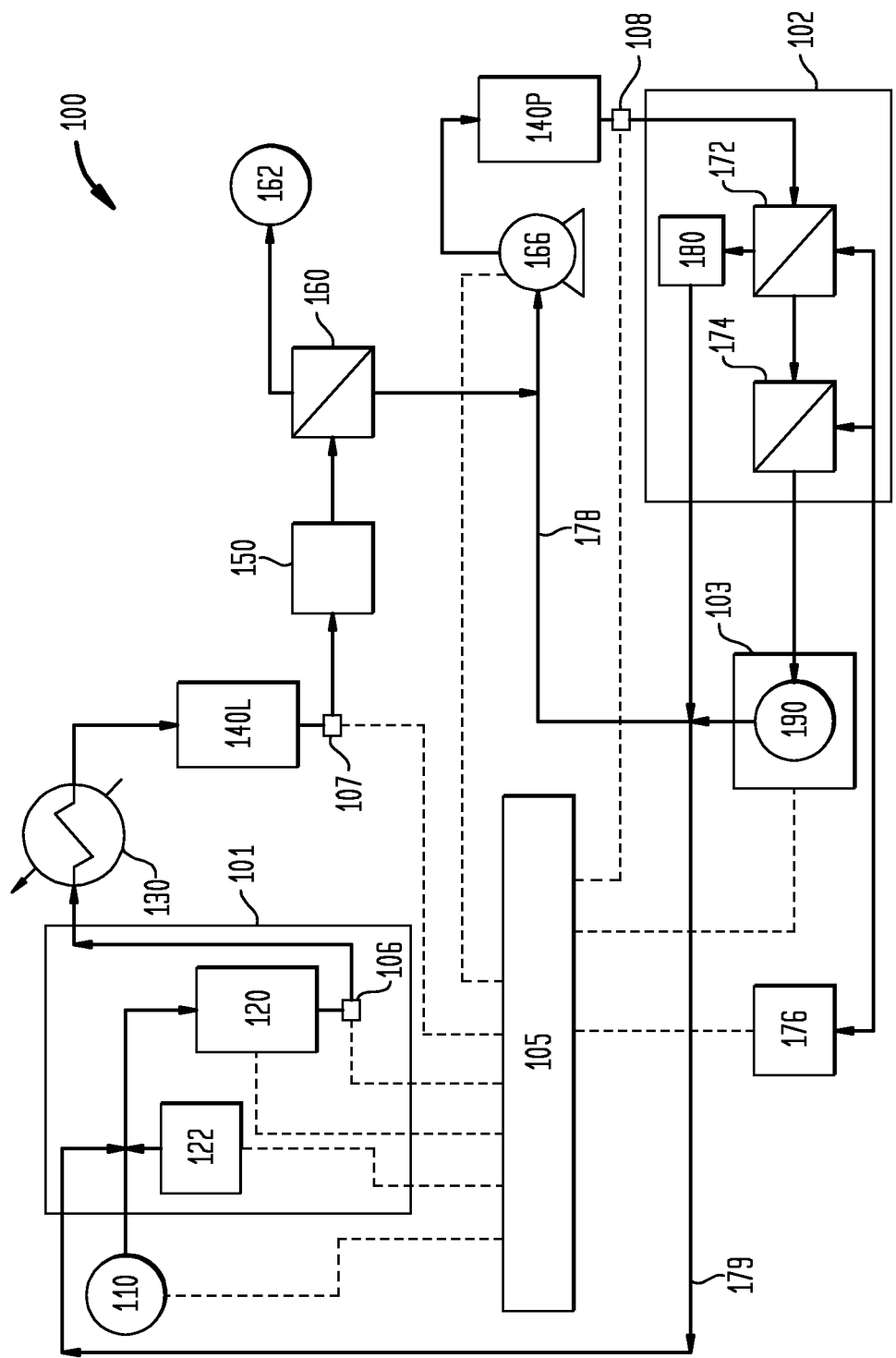
FIG. 1 is a schematic drawing illustrating a system in accordance with one or more embodiments.

One or more aspects can be directed to water treatment or purification systems and techniques. The various systems and techniques typically utilize or comprise one or more unit operations that remove undesirable species from a process fluid or stream. A plurality of unit operations may be utilized serially or in parallel flow arrangement, or a combination of serial and parallel flow arrangement, to facilitate non-selective or selective removal or a reduction of concentration or level of a variety of target species or compounds, which are typically undesirable or objectionable, in a process stream. Further, the systems and techniques may utilize one or more unit operations to facilitate adjustment of a concentration of a species or a byproduct species generated from a unit operation of the system. Some aspects can be directed to techniques and systems or components thereof that treat or purify water that, in some cases, can be characterized as having a low level of impurities or contaminants. Some advantageous aspects can be directed to systems and techniques that provide ultrapure water. Particularly advantageous aspects can be directed to systems and techniques that provide ultrapure water for use in semiconductor processing or fabrication operations. Some aspects and embodiments provide systems and techniques that provide make-up water in a circulating water or ultrapure water system in a manner that maintains a water or ultrapure water characteristic of the water circuit containing water or ultrapure water. The systems and techniques may, in some cases, co-mingle make-up or inlet water or ultrapure water with treated water or ultrapure water. Still further aspects can be directed to control systems and techniques suitable for use with water treatment or purification systems. Even further aspects can be directed to control systems and techniques that facilitate semiconductor fabrication operations by providing ultrapure water. Indeed, some aspects may be directed to control systems and techniques that facilitate water or ultrapure water treatment or purification by utilizing a feedforward or a feedback approach or both. Even further aspects can be directed to techniques for measuring a level or concentration of a target species or compound in the water or ultrapure water or a liquid stream. The measuring techniques may utilize control systems and techniques that facilitate providing ultrapure water.

In accordance with at least one aspect, some embodiments thereof can involve a system for treating water. The system and techniques can involve a first process train that relies on utilizing purified water to create conditions that are conducive to free radical scavenging along with one or more ancillary process trains with unit operations that remove or at least reduce the concentration of byproducts of upstream processes. The system for treating water can comprise at least one free radical scavenging system fluidly connected to at least one source of water that can contain byproducts from one or more upstream processes. In certain aspects, the at least one source of water can be pure, or even ultrapure, and preferably water having a resistivity of at least 15 megohm cm. The system for treating water can also comprise, or be fluidly coupled to, at least one particulate removal system that is fluidly connected downstream of the at least one free radical scavenging system and at least one ultrapure water delivery system that is fluidly connected downstream of at least one particulate removal system. Further the system for treating water typically also comprises at least one water return system that fluidly connects the at least one ultrapure water delivery system to at least one of the free radical scavenging systems. The free radical scavenging system, in some cases, can consist essentially of, or preferably, comprise at least one source of at least one precursor compound. Typically, the at least one source of at least one precursor compound is disposed or otherwise constructed and arranged to introduce at least one free radical precursor compound into at least a portion of the water from the at least one source of water. The free radical scavenging system can further consist essentially of or comprise at least one source of actinic radiation with or without at least one further alternative apparatus that can also initiate or convert at least one precursor compound into at least one free radical scavenging species in the water. In still other cases, the particulate removal system can comprise at least one ultrafiltration apparatus. Typically, at least one ultrafiltration apparatus is fluidly connected downstream of the at least one source of actinic radiation or at least one free radical initiating apparatus and, preferably, upstream of at least one ultrapure water delivery system.

In accordance with at least one further aspect, some embodiments thereof can involve a system for providing ultrapure water to a semiconductor fabrication unit. The system can comprise one or more sources of water fluidly connected to at least one actinic radiation reactor. The at least one reactor is preferably configured to irradiate water from the source of water. The system can further comprise one or more sources of a precursor compound. The one or more sources of precursor compound can be disposed to introduce one or more free radical precursor compounds into the water from the one or more water sources.

The actinic radiation reactor may be a reactor including one or multiple ultraviolet (UV) lamps that produce ultraviolet light that, when absorbed by the free radical precursor compound, causes free radicals to be produced from the free radical precursor compound. The free radicals may oxidize dissolved organic carbon species in the water, for example, trichloromethane or urea, into less undesirable chemical species, for example, carbon dioxide and water. Embodiments of a treatment process for removing undesirable species, for example, organic carbon species from a fluid, for example, water, may be referred to herein an Advanced Oxidation Process (AOP) or a free radical scavenging process. These terms are used synonymously herein.

The system can also comprise at least one particulate filter fluidly connected downstream of at least one of the one or more actinic radiation reactors and, preferably, upstream of an ultrapure water distribution system. The ultrapure water distribution system is, in some advantageous embodiments, fluidly connected to the semiconductor fabrication unit. The water source typically provides water having a total organic carbon (TOC) value of less than about 25 ppb. The system for providing ultrapure water can further comprise a recycle line that fluidly connects the ultrapure water distribution system, typically an outlet port thereof, with the at least one of the source of water, the actinic radiation reactor, and the particulate filter.

In accordance with some aspects, some embodiments can involve a method of providing ultrapure water to a semiconductor fabrication unit. The method can comprise one or more acts of providing inlet water having a TOC value of less than about 25 ppb, introducing at least one free radical precursor compound into the water, and converting the at least one free radical precursor compound into at least one free radical scavenging species. The method can further comprise one or more acts of removing at least a portion of any particulates from the water to produce the ultrapure water, and delivering at least a portion of the ultrapure water to the semiconductor fabrication unit.

In accordance with other aspects, some embodiments can involve a computer-readable medium having computer-readable signals stored thereon that define instructions that as a result of being executed by at least one processor, instruct the at least one processor to perform a method of regulating addition of at least one free radical precursor compound into an inlet water. The inlet water, in some cases, can be pure or ultrapure water, but preferably has a TOC value of less than about 25 ppb. The method executable by the at least one processor can comprise one or more acts of generating one or more drive signals based at least partially on the TOC value of the inlet water; and transmitting the one or more drive signals to at least one source of the at least one precursor compound, the at least one source disposed to introduce the at least one precursor compound into the inlet water.

In accordance with other aspects, some embodiments can include a system for treating water. The system can comprise a primary actinic radiation reactor. The system can further comprise a source of a persulfate precursor compound disposed to introduce at least one persulfate precursor compound into the primary actinic radiation reactor. The system can further comprise one or more sensors such as a total organic carbon (TOC) concentration sensor located upstream of the primary actinic radiation reactor. The system can further comprise a persulfate concentration sensor located downstream of the primary actinic radiation reactor. The system can further comprise a source of a reducing agent. The reducing agent can be disposed to introduce at least one reducing agent downstream of the primary actinic radiation reactor. A reducing agent concentration sensor can also be provided. The reducing agent concentration sensor can be located downstream of a point of addition of the at least one reducing agent. A controller can also be provided. The controller can be operatively coupled to receive at least one input signal from at least one of the TOC concentration sensor, the persulfate concentration sensor, and the reducing agent concentration sensor. The controller can regulate at least one of a rate at which the persulfate precursor compound is introduced into the primary actinic radiation reactor, an intensity of the actinic radiation in the primary actinic radiation reactor, and a rate at which the reducing agent is introduced to the system.

In accordance with yet other aspects, a method of treating water is provided. The method can comprise providing water to be treated. The method can also comprise measuring a TOC value of the water to be treated, and introducing persulfate anions to the water to be treated based at least in part on at least one input signal of the measured TOC value of the water to be treated. The method can also comprise introducing the water containing persulfate anions to a primary reactor, and exposing the persulfate anions in the water to ultraviolet light in the reactor to produce an irradiated water stream. The method can further comprise adjusting an intensity of the ultraviolet light based at least in part on at least one of an input signal selected from the group consisting of a TOC value of the water to be treated, a persulfate value of the water downstream of the reactor, and a rate of addition of persulfate anions. A reducing agent can be introduced to the irradiated water.

In accordance with yet other aspects, a method for measuring a concentration of a compound in a liquid stream is provided. The method can comprise measuring a first conductivity in the liquid stream, and irradiating at least a portion of the liquid stream. The method can further comprise measuring a second conductivity of the liquid stream after irradiating, and calculating the concentration of the compound based at least in part on the first conductivity measurement and the second conductivity measurement. In certain embodiments, the compound can be persulfate or sulfur dioxide.

In accordance with yet other aspects, a method for controlling introduction of sulfur dioxide to a liquid stream is provided. The system can comprise a persulfate concentration sensor in fluid communication with the liquid stream. The system can further comprise a source of sulfur dioxide. The sulfur dioxide can be disposed to introduce sulfur dioxide to the liquid stream downstream of the persulfate concentration sensor. The system can further comprise a sulfur dioxide concentration sensor in fluid communication with the liquid stream and located downstream of the source of sulfur dioxide. The system can further comprise a controller. The controller can be configured to generate a control signal that regulates at least one of a rate of addition of and an amount of the sulfur dioxide introduced into the liquid stream based on at least one input signal from any one of the persulfate concentration sensor and the sulfur dioxide stream.

In accordance with yet other aspects, an actinic radiation reactor is provided. The actinic radiation reactor can comprise a vessel, and a first array of tubes in the vessel. The first array of tubes can comprise a first set of parallel tubes, and a second set of parallel tubes. Each tube can comprise at least one ultraviolet lamp and each of the parallel tubes of the first set is positioned to have its longitudinal axis orthogonal relative to the longitudinal axis of the tubes of the second set.

In one or more embodiments, any of which may be relevant to one or more aspects, the systems and techniques disclosed herein may utilize one or more subsystems that adjusts or regulates or at least facilitates adjusting or regulating at least one operating parameter, state, or condition of at least one unit operation or component of the system or one or more characteristics or physical properties of a process stream. To facilitate such adjustment and regulatory features, one or more embodiments may utilize controllers and indicative apparatus that provide a status, state, or condition of one or more components or processes. For example, at least one sensor may be utilized to provide a representation of an intensive property or an extensive property of, for example, water from the source, water entering or leaving the free radical scavenging system, water entering or leaving the particulate removal system, or water entering or leaving an actinic radiation reactor or one or more other downstream processes. Thus, in accordance with a particularly advantageous embodiment, the systems and techniques may involve one or more sensors or other indicative apparatus, such as composition analyzers, or conductivity cells, that provide, for example, a representation of a state, condition, characteristic, or quality of the water entering or leaving any of the unit operations of the system.

FIG. 1 schematically embodies a system 100 in accordance with one or more aspects. System 100 can be representative of a water treatment or purification system that provides water including water that can be considered to be ultrapure water. In some particularly advantageous embodiments, system 100 can be directed to or be representative of a purification system providing ultrapure water suitable for use in semiconductor fabrication facilities or at least maintaining an ultrapure water quality. Still further aspects involve a system 100 that can be considered as utilizing ultrapure water to provide treated ultrapure water to one or more semiconductor fabrication units (not shown). Thus, in accordance with some aspects, system 100 can be a water treatment system that reduces a concentration, content, or level of one or more impurities or contaminants that may be present in make-up or inlet water from one or more water sources 110 and provide the treated water to a system that utilizes ultrapure water.

As exemplarily illustrated, system 100 can comprise one or more first or primary treatment trains or systems 101 coupled to one or more second or secondary treatment trains or systems 102. System 100 may further comprise at least one water distribution system 103 fluidly connected to at least one secondary treatment system and, in some even more advantageous configurations, to at least one primary treatment system. Further advantageous embodiments can involve configurations that involve at least one flow directional control device in at least one of the primary treatment system, the secondary treatment system, and the water distribution system. Non-limiting examples of directional flow control devices include check valves and weirs.

Preferably, source 110 provides water consisting of, consisting essentially of, or comprising a low level of impurities. More preferably, water from source 110 consists of, consists essentially of, or comprises ultrapure water having at least one characteristic selected from the group consisting of a total organic carbon level or value of less than about 25 ppb or even less than about 20 ppb, as urea, and a resistivity of at least about 15 megohm cm or even at least about 18 megohm cm. First or primary treatment system 101 can further comprise at least one source 122 of a precursor treating compound fluidly connected to reactor 120.

Water introduced into system 100 from source 110 typically, or even preferably, can be characterized by having a low level of impurities. For example, some embodiments utilize pure or ultrapure water or mixtures thereof that have previously been treated or purified by one or more treatment trains (not shown) such as those that utilize reverse osmosis, electrodialysis, electrodeionization, distillation, ion exchange, or combinations of such operations. As noted, advantageous embodiments involve ultrapure inlet water from source 110 that typically has low conductivity or high resistivity of at least about 15 megohm cm, preferably at least about 18 megohm cm, and/or has a low level of contaminants as, for example, a low total organic carbon level of less than about 50 ppb, and preferably, less than about 25 ppb, typically as urea or other carbon compound or surrogate. In certain embodiments, the inlet water may be as low as 1 ppb. In other embodiments, the inlet water may be as low as 0.5 ppb. In yet other embodiments, the resistivity of the inlet water may be about 1 megohm cm.

In some particular embodiments, first treatment system 101 can be characterized or comprise at least one free radical scavenging system. The free radical scavenging system 101 can comprise at least one free radical scavenger reactor 120, such as an irradiation reactor, fluidly connected to at least one source 110 of water. Reactor 120 can be a plug flow reactor or a continuously stirred tank reactor, or combinations thereof. In certain embodiments, a plug flow reactor can be used to prevent the likelihood of blinded or regions of lower irradiation intensity, such as short circuiting, of illumination by the lamps within the reactor. A plug flow reactor can be defined as a reactor that operates under conditions that facilitate laminar flow paths of fluid through the reactor, having parallel, non-turbulent flow paths. Reactor 120 is typically sized to provide a residence time sufficient to allow free radical species in the water flowing in the reactor to scavenge, degrade, or otherwise convert at least one of the impurities, typically the organic carbon-based impurities into an inert compound, one or more compounds that may be removed from the water, or at least to one that can be more readily removed relative to the at least one impurity.

The reactor can additionally be sized based on the expected flow rate of the system to provide a sufficient or a desired residence time in the reactor. In certain embodiments, the flow rate of water through the system can be based on the demand for treated water downstream of the system, or the flow rate of water being utilized upstream of the system, or both. In certain examples, the flow rate of water through the system, or through each reactor, can be between about 1 gallon per minute (gpm) and 2000 gpm. In particular examples, the flow rate can be from about 400 gpm to about 1300 gpm. In other particular examples, the flow rate can be from about 400 gpm to about 1900 gpm. The reactor and other unit operations and equipment of the system, such as pumps and flow valves, can be selected and sized to allow for fluctuations or changes in flow rates from about 400 gpm to about 1900 gpm.

In the free radical scavenging system, organic compounds in the water can be oxidized by one or more free radical species into carbon dioxide, which can be removed in one or more downstream unit operations. Reactor 120 can comprise at least one free radical activation device that converts one or more precursor compounds into one or more free radical scavenging species. For example, reactor 120 can comprise one or more lamps, in one or more reaction chambers, to irradiate or otherwise provide actinic radiation to the water and divide the precursor compound into the one or more free radical species.

The reactor can be divided into two chambers by one or more baffles between the chambers. The baffle can be used to provide mixing or turbulence to the reactor or prevent mixing or promote laminar, parallel flow paths through the interior of the reactor, such as in the chambers. In certain embodiments, a reactor inlet is in fluid communication with a first chamber and a reactor outlet is in fluid communication with a second chamber.

In some embodiments, at least three reactor chambers, each having at least one ultraviolet (UV) lamp disposed to irradiate the water in the respective chambers with light of about 185 nm, 220 nm, and/or 254 nm, or ranging from about 185 nm to about 254 nm, at various power levels, are serially arranged in reactor 120. It is to be appreciated that the shorter wavelengths of 185 nm or 220 nm may be preferable in AOP processes because UV light at these wavelengths has sufficient photon energy to create free radicals from free radical precursors utilized in the process for oxidizing dissolved organic contaminants. In contrast, disinfection processes, where UV light may be utilized to kill or disable microorganisms, may operate efficiently with UV light at the 254 nm wavelength produced by low pressure lamps. Disinfection systems would not typically utilize the more expensive medium pressure or high pressure UV lamps capable of providing significant UV intensity at the shorter 185 nm or 220 nm wavelengths.

Sets of serially arranged reactors can be arranged in parallel. For example, a first set of reactors in series may be placed in parallel with a second set of reactors in series, with each set having three reactors, for a total of six reactors. Any one or more of the reactors in each set may be in service at any time. In certain embodiments, all reactors may be in service, while in other embodiments, only one set of reactors is in service.

Commercially available sources of actinic radiation systems as components of free radical scavenging systems include those from, for example, Quantrol, Naperville, Illinois, as the AQUAFINE® UV system, and from Aquionics Incorporated, Erlanger, Kentucky.

As noted, aspects and embodiments disclosed herein are not limited to a single precursor compound and may utilize a plurality of precursor compounds. In certain embodiments, the precursor compound may be used to degrade an undesirable species. In other embodiments, the precursor compound may be used convert an undesirable component to a removable constituent, such as an ionized species, or a weakly charged species. A plurality of precursor compounds may be utilized to generate a plurality of free radical species. This complementary arrangement may be advantageous in conditions where a first free radical scavenging species selectively degrades a first type of undesirable compound and a second free radical species selectively degrades other undesirable compounds. Alternatively, a first precursor compound may be utilized that can be readily converted to a first converted species or a first free radical species. The first free radical species can then convert a second precursor compound into a second converted species or a second free radical species. This cascading set of reactions may also be advantageous in conditions where the first free radical species selectively degrades or converts a first type of undesirable compound and the second free radical species selectively degrades or converts other undesirable compounds or in cases where conversion or activation of the second precursor compound into the second free radical species undesirably requires high energy levels. A plurality of compounds may be used to provide a plurality of scavenging species.

The one or more precursor compounds can be any compound that can be converted to or facilitates conversion of a free radical scavenging species. Non-limiting examples include persulfate salts such as alkali and alkali metal persulfates and ammonium persulfate or ammonium persulfate, hydrogen peroxide, peroxide salts such as alkali and alkali metal peroxides, perborate salts such as alkali and alkali metal perborates, peroxydisulfate salts such as alkali and alkali metal peroxydisulfate and ammonium peroxydisulfate, acids such as peroxydisulfuric acid, peroxymonosulfuric acid or Caro's acid, and ozone, as well as combinations thereof such as piranha solution. The amount of the one or more precursor compounds can vary depending on the type of contaminant. The precursor compound can consist of or consist essentially of ammonium persulfate which may be advantageous in semiconductor fabrication operations because it would likely provide byproducts that are not considered contaminants of such operations or because they can be readily removed by, for example, ion exchange systems, in contrast to precursor compounds comprising sodium persulfate which can produce sodium species that are not readily removable and/or can undesirably contaminate a semiconductor device.

In some cases, system 100 can comprise at least one degasifier 160 and, optionally, at least one particulate filter downstream of reactor 120. In some cases, system 100 can further comprise at least one apparatus that removes at least a portion of any ionic or charged species from the water. For example, system 100 in one or both of scavenging system 101 or particulate removal system 102 can comprise a bed of ion exchange media or an electrically-driven ion purification apparatus, such as an electrodialysis apparatus or an electrodeionization apparatus. In particularly advantageous configurations, system 100 can comprise a first, primary or leading ion exchange column 140L comprising an ion exchange resin bed and a second, lagging or polishing ion exchange column 140P, also comprising ion exchange resin bed, each serially disposed, relative to each other, along a flow path of the water through system 100. The ion exchange columns may comprise a mixed bed of anion exchange media and cation exchange media. Other configurations, however, may be utilized. For example, lead ion exchange column 140L may comprise serially arranged layers or columns; the first layer or column can predominantly comprise anion exchange media and the second column can predominantly comprise cation exchange media. Likewise, although polish column 140P can comprise a mixed bed of anion exchange media and cation exchange media, polish column 140P may comprise serially arranged layers of columns of a type of exchange media; the first column can predominantly comprise anion exchange media and the second column can predominantly comprise cation exchange media. Any of the first and second layers or columns may be disposed within a single vessel comprising 140L or 140P and be practiced as layered beds of media contained within the columns. The ion exchange media in ion exchange columns 140L and 140P may be any suitable resin including those that remove sulfate species, carbon dioxide, and ammonia or ammonium and any other undesirable species or contaminant in the water from source 110 or as a byproduct of the free radical scavenging process. The ion exchange columns can be mixed bed ion exchange columns that contain anionic and cationic resin.

Commercially available media or ion exchange resins that may be utilized include, but are not limited to, NR30 MEG PPQ, USF™ MEG PPQ, and USF™ NANO resins from Siemens Water Technologies Corp., Warrendale, Pennsylvania, and DOWEX® resin from The Dow Chemical Company, Midland, Michigan.

In some further embodiments, second treatment system 102 can comprise or be characterized as a particulate removal system. For example, system 100 can further comprise at least one particulate filter 150. Filter 150 typically comprises a filtering membrane that removes or traps particles of at least a target size. For example, filter 150 can be constructed with filtering media or one or more membranes that trap all or at least a majority of particles with an average diameter of at least about 10 microns, in some cases, at least about 1 micron, in still other cases, at least about 0.05 micron, and even other cases, at least about 0.02 micron, depending on the service requirements of the point of use connected to the distribution system 103. Filter 150 can comprise a cartridge filter with a membrane that retains particles that are greater than about 0.01 micron.

A particulate filter (not shown) may optionally be utilized to remove particulates introduced with the one or more precursor compounds from source 122. This filter, like filter 150 may also remove particulates greater than 0.02 micron.

In some cases, particulate removal system 102 can comprise one or more ultrafiltration apparatus 172 and 174, each comprising a membrane that prevents particles having an undesirable size characteristic from flowing into the water distribution system with product water. Preferably at least two ultrafiltration apparatus are serially arranged to facilitate removing particulates of, for example, greater than about 0.1 micron, and in some cases, greater than 0.05 micron, and still other cases, greater than 0.02 micron. For example, the ultrafiltration apparatus 172 and 174 may comprise membranes that reduce or otherwise provide a target or desired concentration of particulates larger than 0.05 micron to a level of less than about 100 counts per liter of product water to the point of use. The construction and arrangement of the ultrafiltration apparatus 172 and 174 may depend on the target particulate concentration and the size of the particulates in the ultrapure water product. In some embodiments, filter 172 removes at least a majority of the particulates of target size and filter 174 serves as a polish to ensure that the concentration of particulates to water distribution system 103 is at a level that is less than or equal to the target or desired particulate concentration. In such configurations, a retentate water stream from filter 172 typically contains a majority of the trapped particulates and can be discharged or discarded or used in other processes. Preferably, however, at least a portion of the retentate water stream is introduced into a particulate filter 180 comprising a membrane or media that traps at least a portion of the particulates; the permeate stream therefrom, from which a substantial portion of particulates is removed, can be directed to and mixed with an upstream unit operation of the system 100 such as, but not limited to, a returning or circulating unused ultrapure product water from distribution system 103, inlet water from source 110 introduced into the free radical scavenging system 101, at least partially treated water from reactor 120, filter 150, degasifier 160, lead ion exchange column 140L or polish ion exchange column 140P, or combinations thereof. Like filter 150, filter 180 can also be constructed to remove or reduce a level of particulate material of a certain size to a particular or target level.

Degasifier 160 can comprise a membrane contactor or any unit operation that reduces a concentration of any dissolved gases in the water or other gaseous byproduct of the precursor compound. Preferably, the degasifier reduces any of the dissolved oxygen content, the dissolved nitrogen content, and the dissolved carbon dioxide content in the water. Typically, degasifier 160 utilizes a contacting membrane and a vacuum source 162 that facilitates removal of the dissolved gases from the water. Non-limiting examples of degasifiers that may be utilized herein includes those commercially available as LIQUI-CEL® membrane contactors from Membrana, Charlotte, North Carolina.

Other ancillary unit operations may be utilized to adjust at least one intensive or extensive property of the water provided to a point of use, which can be the semiconductor fabrication unit. For example, a heat exchanger, such as a chiller 130, may be disposed upstream of ultrapure water distribution system 103 to reduce the temperature of at least a portion of the ultrapure water deliverable to at least one semiconductor fabrication unit. As illustrated, chiller 130 is disposed downstream of reactor 120 but upstream of degasifier 160. Aspects and embodiments disclosed herein, however, are not limited to the exemplary presented arrangement and one or more heat exchangers may be, for example, in thermal communication with the ultrapure water product downstream of particulate removal system 102 but upstream of water distribution system 103. Indeed, a plurality of heat exchangers may be utilized. For example, a first heat exchanger, such as a heater, may heat the water having at least one free radical precursor compound to assist in initiating or converting the precursor compound into one or more free radical scavenging species and a second heat exchanger, such as a chiller, may cool the treated ultrapure water prior to delivery through the water distribution system.

Still other ancillary systems include, for example, one or more pumps 166 that provide motive force for circulating the water through system 100. Pump 166 may be a positive displacement pump or a centrifugal pump. Preferably, pump 166 comprises components that do not undesirably contribute to the contamination characteristics of the product water.

Water distribution system 103 can comprise an inlet port and at least one outlet port fluidly connected to and providing ultrapure product water to one or more points of use (not shown), such as one or more semiconductor fabrication units.

In some cases, for example, the water distribution system comprises a manifold 190 having an inlet port fluidly connected to free radical scavenging system 101, particulate removal system 102, or both, and at least one product outlet fluidly connected to at least one point of use, and at least one return outlet port fluidly connected to one or more circulating systems 178 and 179 to recycle unused product water to one or both of the free radical scavenging system and the particulate removal system or into any point in system 100.

Figure 2:
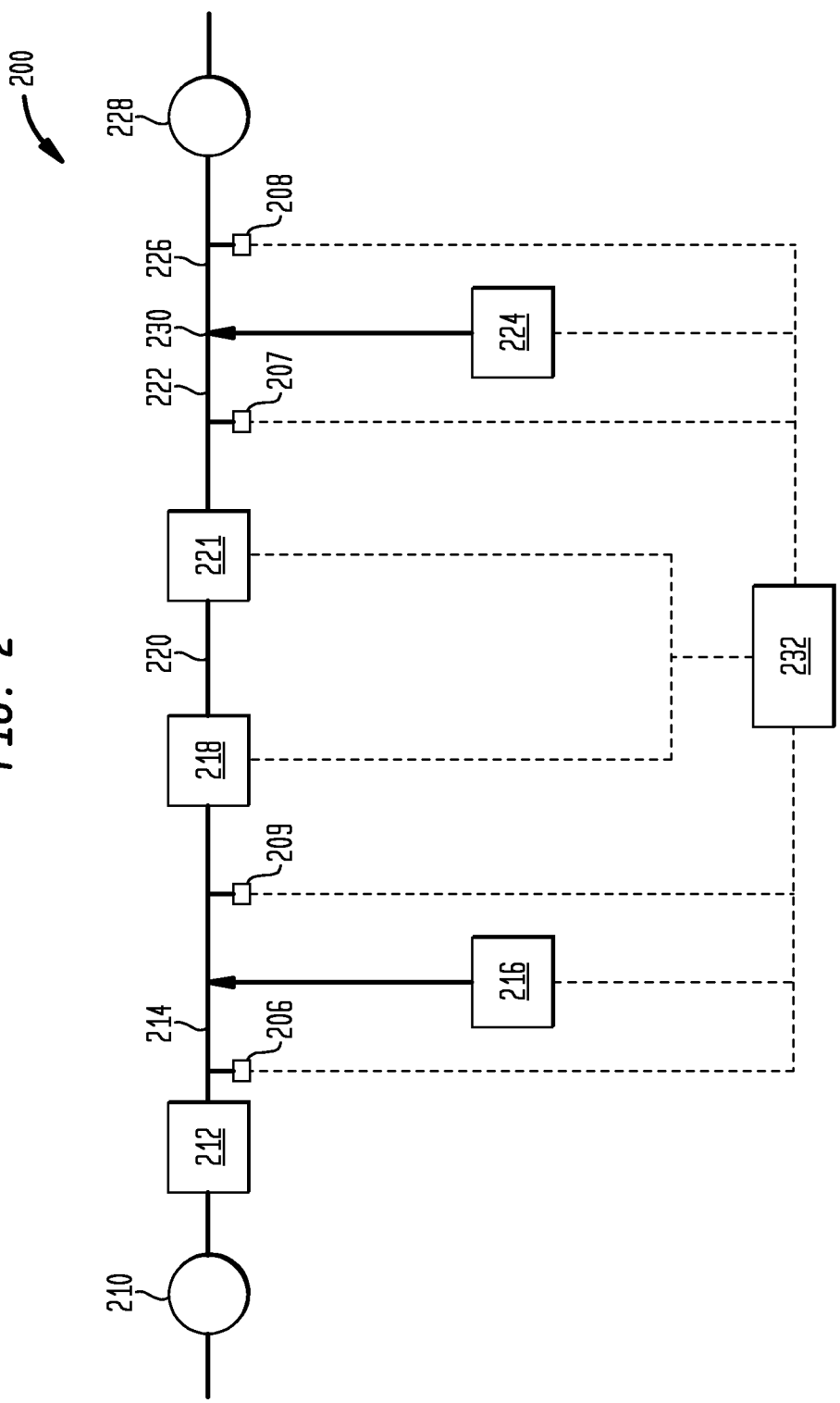
FIG. 2 is a schematic drawing illustrating a system in accordance with one or more embodiments.

FIG. 2 schematically embodies a system 200 in accordance with one or more aspects. System 200 can be representative of a water treatment or purification system that provides water including water that can be considered to be ultrapure water. In some particularly advantageous embodiments, system 200 can be directed or be representative of a purification system providing ultrapure water suitable for semiconductor fabrication facilities or at least maintaining an ultrapure water quality. Still further aspects involve a system 200 that can be considered as utilizing ultrapure water to provide treated ultrapure water to one or more semiconductor fabrication units (not shown). In yet further aspects, system 200 can be directed to or be representative of a purification system providing ultrapure water suitable for processing by system 100 of FIG. 1, or at least a part of a system that can provide ultrapure water. Thus, in accordance with some aspects, system 200 can be a water treatment system that reduces a concentration, content, or level of one or more impurities or contaminants that may be present in make-up or inlet water from one or more water sources 210 and provide the treated water to a system that utilizes ultrapure water.

As with system 100, treatment system 200 can comprise subsystems or components that converts or renders at least a portion of one or more target species into a species that can be removed in any one or more separation unit operations such as, but not limited to, degasification systems, particulate removal systems, and ion trapping, capturing or exchanging systems.

As exemplarily illustrated, system 200 can comprise a series of unit operations 212, 214, and 216. Water to be treated from source of water 210 can be optionally introduced to a reverse osmosis unit to remove particulates from the water stream. Precursor compounds from source 216 of precursor compounds can be introduced into filtrate 214 from reverse osmosis unit 212. The filtrate stream with the precursor compounds disposed therein can be introduced into free radical scavenging system 218. Free radical scavenging system 218 can comprise at least one free radical scavenger reactor or actinic radiation reactor fluidly connected to at least one source 210 of water.

Free radical scavenging system 218 can comprise one or more reactors or vessels, each of which can be arranged serially or in parallel. In certain embodiments, sets of serially arranged reactors can be arranged in parallel. For example, a first set or train of reactors in series may be placed in parallel with another set or train of reactors, also in series, with each set having three reactors, for a total of six reactors in free radical scavenging system 218. Any one or more of the reactors in each set may be in service at any time. In certain embodiments, all reactors may be in service, while in other embodiments, only one set of reactors is in service. Free radical scavenging system 218 can also be considered a primary actinic radiation reactor.

The reactor can be a plug flow reactor or a continuously stirred tank reactor, or combinations thereof. In certain embodiments, a plug flow reactor can be used so as to prevent or reduce the likelihood of blinded or regions of lower irradiation intensity, such as short circuiting, of illumination by the lamps within the reactor. The reactor is typically sized to provide a residence time sufficient to generate and/or allow free radical species in the water flowing in the reactor to scavenge, degrade, or otherwise convert at least a portion of the at least one of the impurities, typically the organic carbon-based impurities into an inert or ionized compound, one or more compounds that may be removed from the water, or at least to one that can be more readily removed relative to the at least one impurity. The reactor can additionally be sized based on the expected flow rate of the system to provide a sufficient residence time in the reactor. The reactor can also be sized based on the flow rate of water through the system. In certain embodiments, the flow rate of water through the system can be based on the demand for treated water downstream of the system, or the flow rate water being utilized upstream of the system. In certain examples, the flow rate can be between about 1 gallon per minute (gpm) and 2000 gpm. In particular examples, the flow rate can be between about 500 gpm and about 1300 gpm. In other particular examples, the flow rate can be from about 1300 gpm to about 1900 gpm.

In the free radical scavenging system, organic compounds in the water can be oxidized by one or more free radical species into carbon dioxide, which can be removed in one or more downstream unit operations. The reactor can further comprise at least one free radical activation device that converts one or more precursor compounds into one or more free radical scavenging species. For example, the reactor can comprise one or more lamps, in one or more reaction chambers, to irradiate or otherwise provide actinic radiation to the water that activates, converts or divides the one or more precursor compounds into the one or more free radical species.

The reactor can, thus, be sized based on the number of ultraviolet lamps required to scavenge, degrade, or otherwise convert at least one of the impurities, typically the organic carbon-based impurities into an inert, ionized, or otherwise removable compound, one or more compounds that may be removed from the water, or at least to one that can be more readily removed relative to the at least one impurity. The number of lamps required can be based at least in part on lamp performance characteristics including the lamp intensity and spectrum wavelengths of the ultraviolet light emitted by the lamps. The number of lamps required can be based at least in part on at least one of the expected TOC concentration or amount in the inlet water stream and the amount of persulfate added to the feed stream or reactor.

Irradiated water stream 220 can exit free radical scavenging system 218 and can be optionally introduced into a secondary irradiation system which can also include one or more actinic radiation reactors 221. Secondary actinic radiation reactor 221 can comprise one or more vessels, each containing one or more ultraviolet lamps. As with system 218, each of the vessels can be arranged serially or in parallel. In certain embodiments, sets of serially arranged secondary reactors can be arranged in parallel. For example, two or more sets of serially arranged secondary reactors may be placed in parallel, with each set of serially arranged secondary reactors having two or more reactors. Any one or more of the secondary reactors in each set may be in service at any time. In certain embodiments, all secondary reactors may be in service, while in other embodiments, only one set of secondary reactors may be in service. In certain embodiments, the ultraviolet lamps may emit ultraviolet light at a wavelength of in a range of about 185 nm to about 254 nm.

System 200 can have a source of reducing agent 224 which can introduce one or more neutralizing or reducing agents such as sulfur dioxide, to the further irradiated water stream 222 at, for example, point of addition 230. The neutralizing or reducing agent can be any compound or species that can reduce or neutralize any of the residual precursor compounds or derivatives thereof in irradiated water stream 222 to a desired level.

Stream 226 can be introduced to one or more downstream processes 228, or can be used as ultrapure water in a desired application, such as in a semiconductor fabrication process.

In some advantageous embodiments, system 200 can further comprise one or more unit operations that further remove any non-dissolved material, such as particulate filters. A particulate filter such as an ultrafiltration apparatus, may be located downstream from primary actinic radiation reactor 218.

Further advantageous embodiments can involve configurations that involve at least one flow directional control device in the system. Non-limiting examples of directional flow control devices include check valves and weirs.

Any of sources 110 and 210 can provide water consisting of, consisting essentially of, or comprising a low level of impurities. More preferably, water from source 110 or 210 consists of, consists essentially of, or comprises ultrapure water having at least one characteristic selected from the group consisting of a total organic carbon level or value of less than about 25 ppb or even less than about 20 ppb, as urea, and a resistivity of at least about 15 megohm cm or even at least about 18 megohm cm. Free radical scavenging system 101 can further comprise at least one source 122 of a precursor compound fluidly connected to reactor 120.

Water introduced into system 100 and/or system 200 from source 110 and source 210 typically, or even preferably, can be characterized as having a low level of impurities. For example, some embodiments utilize pure or ultrapure water or mixtures thereof that have previously been treated or purified by one or more treatment trains (not shown) such as those that utilize reverse osmosis, electrodialysis, electrodeionization, distillation, ion exchange, or combinations of such operations. As noted, advantageous embodiments involve ultrapure inlet water from, for example, source 110 and/or source 210 that typically has low conductivity or high resistivity, of at least about 15 megohm cm, preferably at least about 18 megohm cm, and/or has a low level of contaminants as, for example, a low total organic carbon level of less than about 50 ppb, and preferably, less than about 25 ppb, typically as urea or other carbon compound, or surrogate thereof.

One or more lamps can be utilized in the reactors to illuminate or irradiate the fluid contained therein. Particular embodiments can involve reactors having a plurality of lamps, each advantageously disposed or positioned therein to irradiate the fluid with one or more illumination intensity levels for one or a plurality of illumination periods. Further aspects can involve utilizing the one or more lamps within any of the reactors in configurations that accommodate or facilitate a plurality of simultaneous illumination intensities.

The ultraviolet lamps can be advantageously positioned or distributed within the one or more reactors of the free radical scavenging system to irradiate or otherwise provide actinic radiation to the water as desired. In certain embodiments, it is desired to distribute the lamps within the one or more reactors to evenly distribute actinic radiation throughout the reactor. In any of systems 218 and reactors 221, the ultraviolet lamps of the free radical scavenging system can be adjusted to provide illumination at various intensities or various power levels. For example, ultraviolet lamps can be used that can be adjusted to operate at a plurality of illumination modes, such as dim, rated, and boost mode, for example, a low, medium, or high mode.

In any of the systems and reactors disclosed herein, the power output of ultraviolet lamps of the free radical scavenging system may be continuously adjusted or dimmed over a range of power levels. The power output of the ultraviolet lamps may be adjustable to provide sufficient power to remove a desired amount of TOC from fluid, e.g., water, undergoing treatment in the systems and reactors disclosed herein while not producing more ultraviolet radiation than is necessary. Such control over the power output of the ultraviolet lamps decreases operating costs by reducing the power output and power consumption of the ultraviolet lamps such that excess, unutilized UV radiation is not produced.

The usable lifetime of a UV lamp is related to the total power output of the UV lamp. For example, one type of UV lamp having a nominal power rating of 4.9 kW exhibits a lifetime of about 4,000 hours when operated at 4.9 kW, a lifetime of about 6,500 hours when operated at 3.5 kW, and a lifetime of about 1,000 hours when operated at 5.8 kW. Operating UV lamps at power levels that are no higher than those sufficient to remove a desired amount of TOC from fluid, e.g., water, undergoing treatment in the systems and reactors disclosed herein may thus extend the lifetime of the UV lamps, further reducing system operating costs by reducing the frequency of UV lamp replacement and number of UV lamps consumed over time and associated UV lamp and labor costs.

Operating an AOP system with continuously dimmable or adjustable power UV lamps may reduce operating costs as compared a system that modulates total UV power applied to a fluid undergoing treatment by selectively turning on or off different UV lamps for an additional reason. It is recognized that each ON-OFF cycle for a high powered UV lamp, such as those used in AOP systems, may reduce lamp lifetime by about 50 hours. Dimming lamps rather than turning them OFF and ON may thus increase lamp lifetimes and decrease replacement costs.

The use of continuously dimmable or adjustable power UV lamps may provide a system with a better response time to changes in TOC than a system that modulates total UV power applied to a fluid undergoing treatment by selectively turning on or off different UV lamps. Typical UV lamps used in AOP processes may require up to five minutes to transition from an OFF state to a state at which they are outputting a rated amount of UV radiation. In comparison, continuously adjustable UV lamp systems as disclosed herein may be capable of substantially instantaneously adjusting output UV radiation intensity. Coupled with a feedback and/or feedforward system that provides measurements of TOC levels in fluid (e.g., water) before and/or after undergoing UV irradiation at a measurement frequency of about 1 minute, 2 minutes-4 minutes, or about 5 minutes to a control system operable to continuously adjust the power output of UV lamps of the treatment system, treatment systems as disclosed herein may provide substantially quicker response to to changes in TOC levels in input liquid than prior known systems. In systems as disclosed herein UV power intensity in treatment reactors may be quickly adjusted in response to changes in TOC concentration of inlet liquid to both avoid undesirable TOC levels in treated fluid and to reduce UV lamp power when not needed to reduce operating costs.

In some embodiments, UV lamps utilized in systems disclosed herein may have a nominal power rating of about 4.5 kW to about 4.9 kW and may be continuously adjustable to operate at a power in a range of from about 2.5 kW to about 5.8 kW. Different embodiments may utilize lamps having different nominal power ratings and continuously adjustable to operate over different power ranges.

Figure 7:
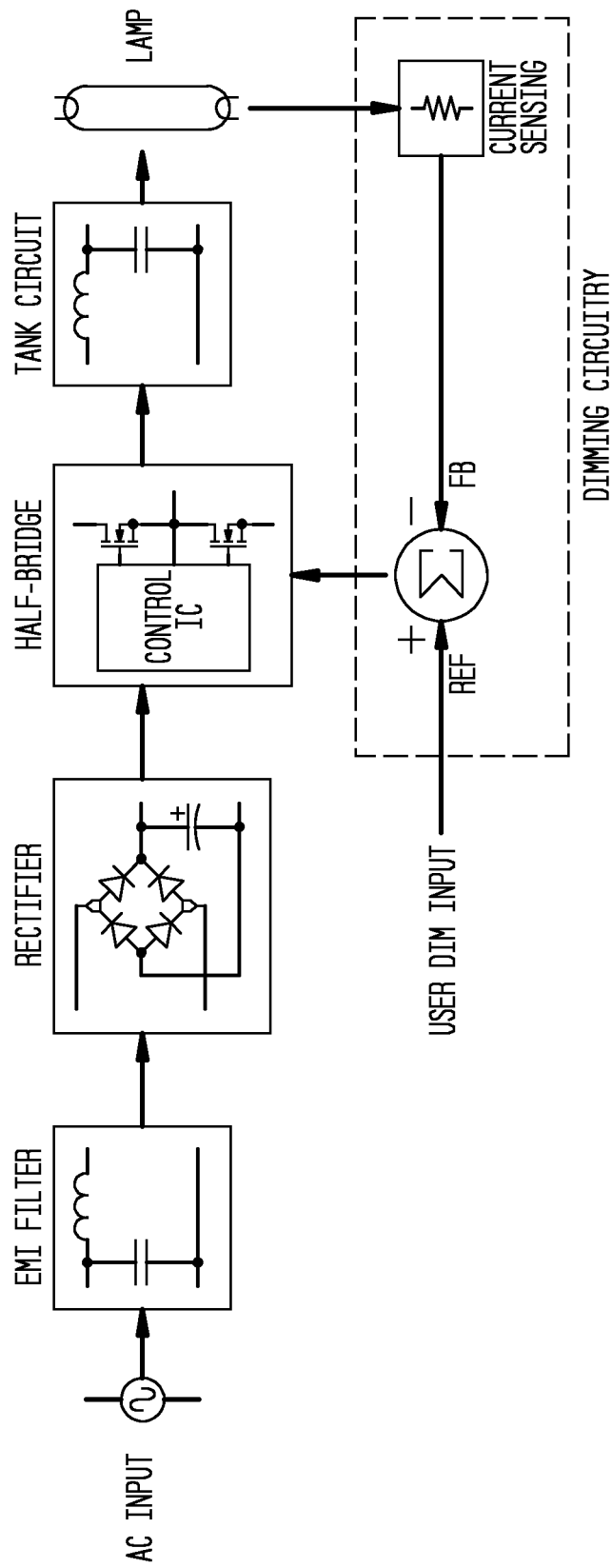
FIG. 7 illustrates a circuit for controlling a continuously variably powered ultraviolet lamp in embodiments of a system in accordance with one or more embodiments.

One embodiment of a circuit that may be utilized to continuously control power provided to a UV lamp utilized in systems disclosed herein is illustrated in FIG. 7. The electronic ballast circuit block diagram in FIG. 7 includes an AC line input voltage source (for example, 120 VAC/60 Hz), an EMI (Electro Magnetic Interference) filter to block circuit-generated switching noise, a rectifier and smoothing capacitor, a control IC and half-bridge inverter for DC to AC conversion, and a resonant tank circuit to ignite and run the lamp. An additional circuit block utilized for dimming is also shown; it includes a feedback circuit for controlling the lamp current.

The lamp requires a current to preheat the filaments, a high voltage for ignition, and a high-frequency AC current during running. To fulfill these requirements, the electronic ballast circuit first performs a low-frequency AC-to-DC conversion at the input, followed by a high-frequency DC-to-AC conversion at the output.

The AC mains voltage is full-wave rectified and then peak-charges a capacitor to produce a smooth DC bus voltage. The DC bus voltage is then converted into a high-frequency, 50% duty-cycle, AC square-wave voltage using a standard half-bridge switching circuit. The high-frequency AC square-wave voltage then drives the resonant tank circuit and becomes filtered to produce a sinusoidal current and voltage at the lamp.

During pre-ignition, the resonant tank circuit is a series-LC circuit with a high Q-factor. The Q, quality factor, of a resonant circuit is a measure of the "goodness" or quality of a resonant circuit. A higher value for this figure of merit corresponds to a narrower bandwidth, which is desirable in many applications. More formally, Q is the ratio of power stored to power dissipated in the circuit reactance and resistance, respectively. After ignition and during running, the tank circuit is a series-L, parallel-RC circuit, with a Q-factor somewhere between a high and low value, depending on the lamp dimming level.

Figure 8:
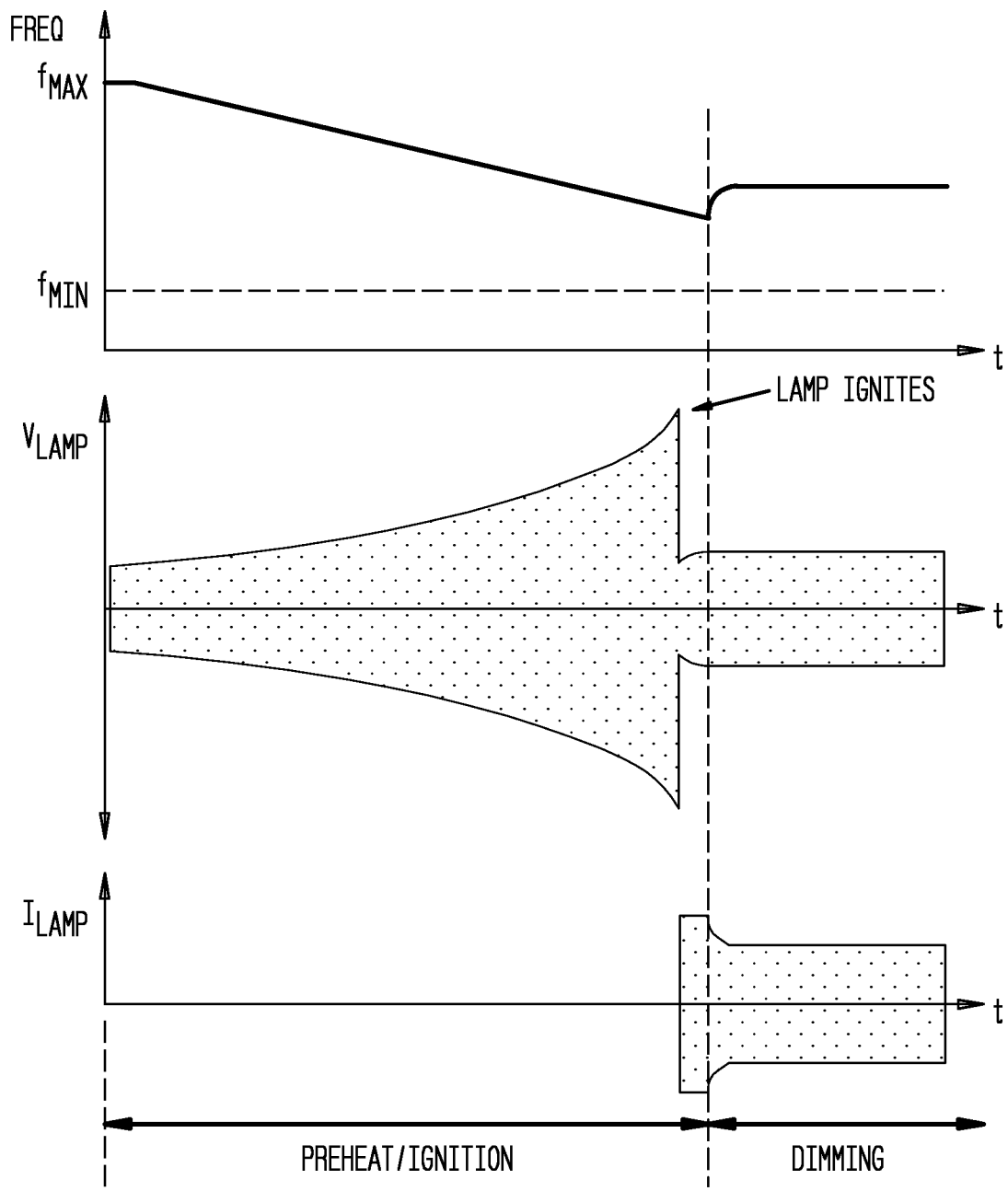
FIG. 8 illustrates electrical parameters associated with ignition and operation of a continuously variably powered ultraviolet lamp in embodiments of a system in accordance with one or more embodiments.

When the UV lamp is first turned on, the control IC sweeps the half-bridge frequency from a maximum frequency down towards the resonance frequency of the high-Q ballast output stage. The lamp filaments are preheated as the frequency decreases and the lamp voltage and load current increase. See FIG. 8.

The frequency keeps decreasing until the lamp voltage exceeds the lamp ignition voltage threshold and the lamp ignites. Once the lamp ignites, the lamp current is controlled such that the lamp runs at the desired power and intensity level.

To dim the UV lamp, the frequency of the half-bridge is increased, causing the gain of the resonant tank circuit to decrease and therefore lamp current to decrease. A closed-loop feedback circuit is then used to measure the lamp current and regulate the current to the dimming reference level by continuously adjusting the half-bridge operating frequency.

The dimming can be controlled either manually or by a low control voltage such as 0-10 VDC. This control voltage can be generated by a total organic carbon (TOC) monitor upstream and/or downstream of an actinic reactor including the continuously dimmable UV lamps so that the UV lamp intensity can be controlled in response to variations in either the AOP feed liquid TOC or effluent TOC.

Figure 3:
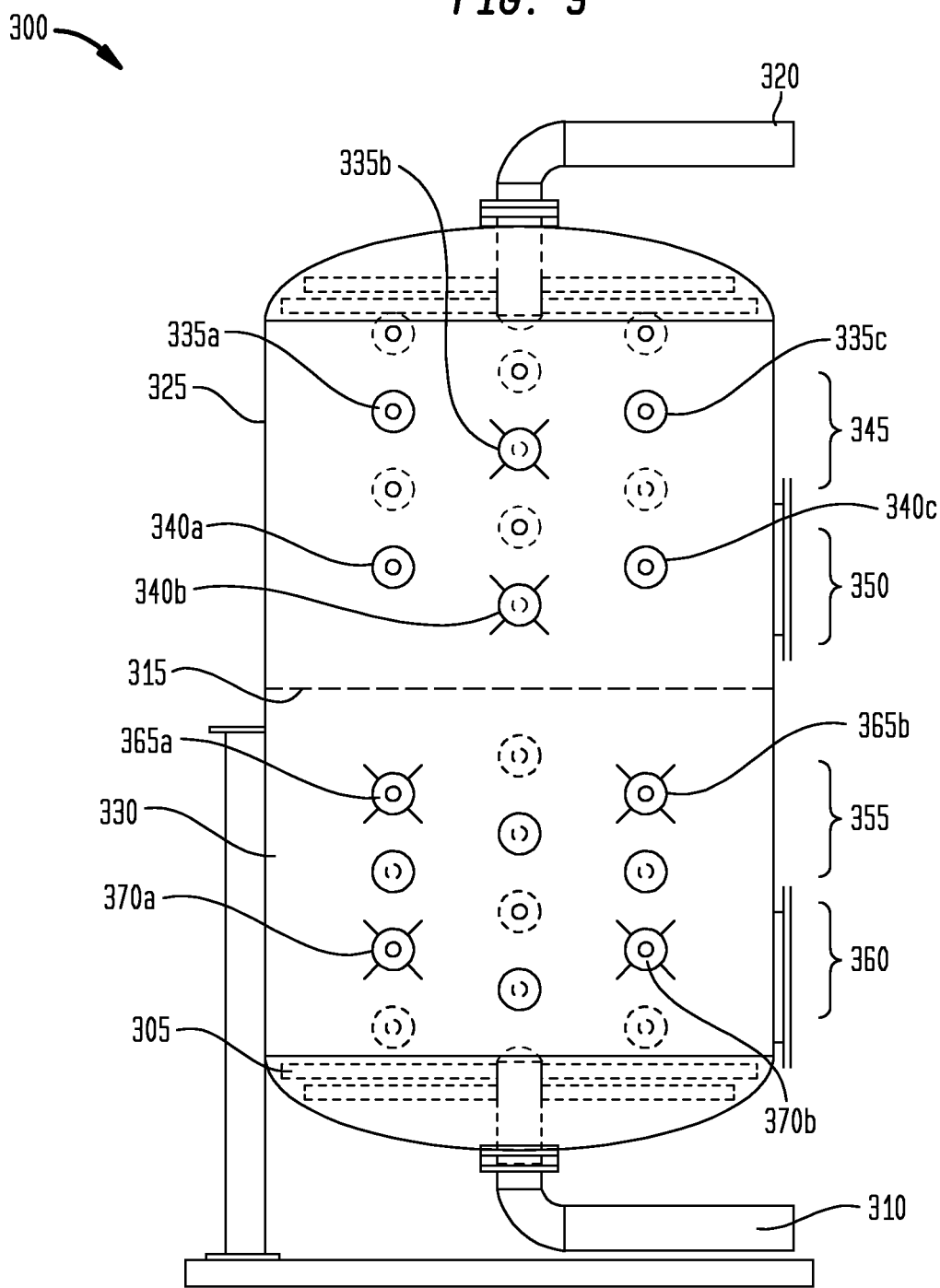
FIG. 3 is a schematic drawing illustrating a vessel in accordance with one or more embodiments.

In some embodiments, different lamps in different portions of an AOP system or reactor may be individually controlled to operate at different power levels and/or to produce different intensities of UV radiation. For example, a subset of UV lamps in a reactor vessel 300 as illustrated in FIG. 3 may be operated at a first power level while a different subset of UV lamps may be operated at a different power level. Multiple subsets of lamps in a reactor vessel 300 may each be operated at different power levels. In systems including multiple reactors, operated in series and/or in parallel, the different reactors may include UV lamps that are operated at different power levels and/or to produce different intensities of UV radiation. For example, in some embodiments, one or more intermediate TOC sensors may be disposed between one or more upstream and one or more downstream reactors. If treatment in the upstream reactor(s) significantly reduces TOC levels in fluid (e.g., water) undergoing treatment, and only minimal further TOC destruction is needed in the downstream reactor(s) to produce a treated water having a desired TOC level, the power levels of the UV lamps in the upstream and/or downstream reactors may be reduced to provide only the UV intensity necessary. In some embodiments, the power levels of the UV lamps in the upstream reactor(s) may be fixed and the power levels of the UV lamps in the downstream reactor(s) continuously adjustable based on a TOC measurement of irradiated water exiting the upstream reactor(s). Similarly, if intermediate TOC sensors indicate that the TOC in irradiated water exiting the upstream reactor(s) is undesirably or unexpectedly high, power levels of UV lamps in the downstream reactor(s) may be increased to a level appropriate to destroy a desired amount of TOC in the irradiated water from the upstream reactor(s)

It is to be appreciated that the dimming circuit shown in FIG. 7 is for illustration purposes only. Aspects and embodiments disclosed herein are not limited by the type of dimming ballast used or to the specific electronic circuitry utilized.

The one or more lamps can be positioned within the one or more actinic radiation reactors by being placed within one or more sleeves or tubes within the reactor. The tubes can hold the lamps in place and protect the lamps from the water within the reactor. The tubes can be made of any material that is not substantially degraded by the actinic radiation and the water or components of the water within the reactor, while allowing the radiation to pass through the material. The tubes can have a cross-sectional area that is circular. In certain embodiments, the tubes can be cylindrical, and the material of construction thereof can be quartz. Each of the tubes can be the same or different shape or size as one or more other tubes. The tubes can be arranged within the reactor in various configurations, for example, the sleeves may extend across a portion of or the entire length or width of the reactor. The tubes can also extend across an inner volume of the reactor.

Commercially available ultraviolet lamps and/or quartz sleeves may be obtained from Hanovia Specialty Lighting, Fairfield, New Jersey, Engineered Treatment Systems, LLC (ETS), Beaver Dam, Wisconsin, and Heraeus Noblelight GmbH of Hanau, Germany. The quartz material selected can be based at least in part on the particular wavelength or wavelengths that will be used in the process. The quartz material may be selected to minimize the energy requirements of the ultraviolet lamps at one or more wavelengths. The composition of the quartz can be selected to provide a desired or suitable transmittance of ultraviolet light to the water in the reactor and/or to maintain a desired or adequate level of transmissivity of ultraviolet light to the water. In certain embodiments, the transmissivity can be at least about 50% for a predetermined period of time. For example, the transmissivity can be about 80% or greater for a predetermined period of time. In certain embodiments, the transmissivity can be in a range of about 80% to 90% for about 6 months to about one year. In certain embodiments, the transmissivity can be in a range of about 80% to 90% for up to about two years.

The tubes can be sealed at each end so as to not allow the contents of the reactor from entering the sleeves or tubes. The tubes can be secured within the reactor so that they remain in place throughout the use of the reactor. In certain embodiments, the tubes are secured to the wall of the reactor. The tubes can be secured to the wall through use of a suitable mechanical technique, or other conventional techniques for securing objects to one another. The materials used in the securing of the tubes is preferably inert and will not interfere with the operation of the reactor or negatively impact the purity of the water, or release contaminants to the water.

The lamps can be arranged within the reactor such that they are parallel to each other. The lamps can also be arranged within the reactor at various angles to one another. For example, in certain embodiments, the lamps can be arranged to illuminate paths or coverage regions that form an angle of approximately 90 degrees such that they are approximately orthogonal or perpendicular to one another. The lamps can be arranged in this fashion, such that they form an approximately 90 degree angle on a vertical axis or a horizontal axis, or any axis therebetween.

In certain embodiments, the reactor can comprise an array of tubes in the reactor or vessel comprising a first set of parallel tubes and a second set of parallel tubes. Each tube may comprise at least one ultraviolet lamp and each of the parallel tubes of the first set can be arranged to be at a desired angle relative to the second set of parallel tubes. The angle may be approximately 90 degrees in certain embodiments. The tubes of any one or both of the first array and the second array may extend across an inner volume of the reactor. The tubes of the first set and the second set can be arranged at approximately the same elevation within the reactor.

Further configurations can involve tubes and/or lamps that are disposed to provide a uniform level of intensity at respective occupied or coverage regions in the reactor. Further configurations can involve equispacially arranged tubes with one or more lamps therein.

The reactor may contain one or more arrays of tubes arranged within the reactor or vessel. A second array of tubes can comprise a third set of parallel tubes, and a fourth set of parallel tubes orthogonal to the third set of parallel tubes, each tube comprising at least one ultraviolet lamp. The fourth set of parallel tubes can also be orthogonal to at least one of the second set of parallel tubes and the first set of parallel tubes.

In certain embodiments, each array within the reactor or vessel can be positioned a predetermined distance or elevation from another array within the reactor. The predetermined distance between a set of two arrays can be the same or different.

Mechanical access to the UV lamps is important since light intensity can decrease over time, rendering it desirable that lamps be replaced when their light output falls below an acceptable level. Chambers or reactors that utilize UV lamps typically have either a single sided or double sided orientation to provide access to the electrical leads that power the lamps. The lamps come in either of these orientations. A single sided lamp may have wiring routed internally back through the lamp and out the single side. Single sided chambers typically are placed where access to both ends of the chamber are not available against walls or where access is too restricted. A double sided lamp has wires in one side and out the other and the chamber they go into have access ports on both sides of the chamber for placing the lamp and for the electrical leads to route through.

Manufacturing costs for nearly identical lamps with only the lead orientation changed are relative to the number of units manufactured. Therefore, if a single part can be produced that can incorporate either orientation it saves on price, stocking quantity, stocking space, lead time issues, and simplify quality control.

In one embodiment, a UV lamp with double sided electrical connections is used in an AOP reactor. To utilize a double sided electrical connection lamp in all reactor chambers, an electrical conductor to connect a source of electricity to either side of the ultraviolet lamp such as a jumper, switch, or short is located on the lamp or leads themselves to route the power and/or ground to one or both sides. Additionally or alternatively, an electrical conductor to connect a source of electricity to the lamp can be located external of the lamp. Aspects and embodiments disclosed herein are not limited to the location or type of electrical connection on the lamp. Utilization of UV lamp with double sided electrical connections simplifies the need for a specific orientation of the reactor chamber. Any electrical switch, jumper, or short can be used as long as it is suitable for the required voltage and amperage. Such a lamp configuration would also allow for a tank or chamber or reactor with a double ended configuration to be placed where access on only one side was available. Panel placement for powering the lamp where lead length was an issue could be resolved with this configuration as well. All this leads to a more flexible apparatus for installation and easier servicing.

Figure 9A:
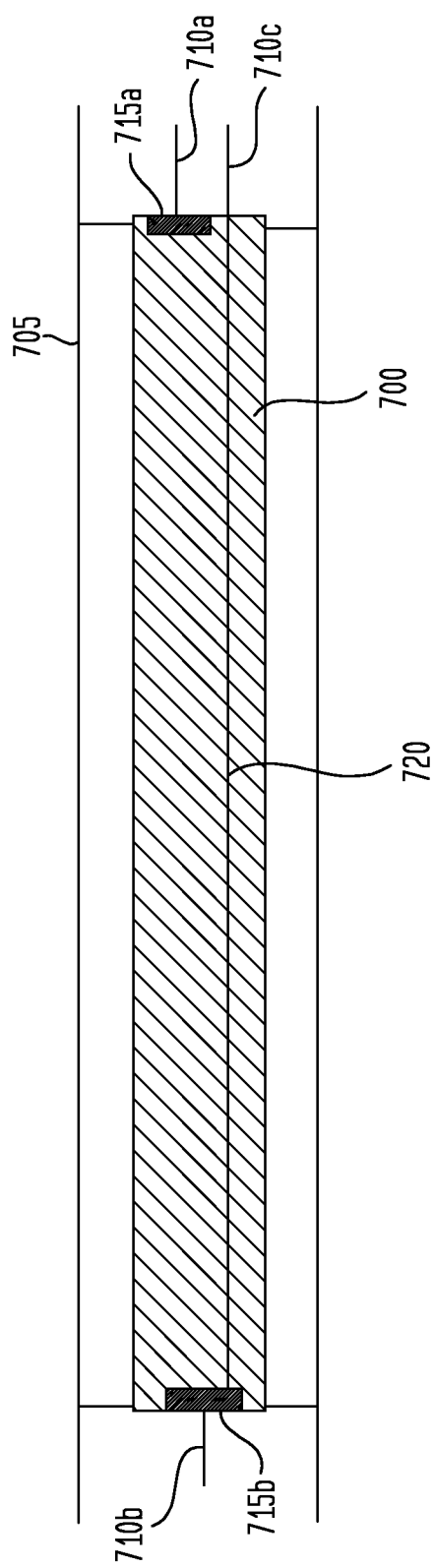
FIG. 9A illustrates an embodiment of a double sided electrical connection lamp utilized in embodiments of a system in accordance with one or more embodiments.

FIG. 9A illustrates one embodiment of a low pressure double sided electrical connection lamp 700 that may be utilized in conjunction with various systems disclosed herein. In some embodiments, lamp 700 is a low pressure UV lamp rated to operate at temperatures of about 100° C. Lamp 700 is illustrated as housed in a quartz sleeve 705 with a double ended configuration with access to the lamp 700 being provided on both ends of the quartz sleeve 705. Lamp 700 includes electrical contacts 710a, 710b, and 710c. Electrical contact 710a is electrically coupled to an electrode 715a on a first side of the lamp 700. Electrical contact 710b is electrically coupled to an electrode 715b on a second side of the lamp. Electrical contact 710c is electrically coupled to the electrode 715b on the second side of the lamp via a conductor 720, for example, a wire, passing internally through the body of the lamp 700. Power may thus be applied to the opposite electrodes 715a, 715b by providing power to contacts 710a and 710b or to contacts 710a and 710c.

FIG. 9B illustrates lamp 700 mounted in sleeve 705 in a dual end entry configuration with electrical connection being made to lamp 700 via electrical conductors 725a and 725b making electrical contact with electrical contacts 710a and 710b, respectively. FIG. 9C illustrates lamp 700 mounted in sleeve 705 in a single end entry configuration in a sleeve 705 having a closed end or only one end through which access to the lamp 700 is available. Electrical connection is made to lamp 700 in FIG. 9C via electrical conductors 725a and 725b making electrical contact with electrical contacts 710a and 710c, respectively. The electrodes 715a, 715b and conductor 720 are omitted from FIGS. 9B and 9C for clarity.

Figure 9D:
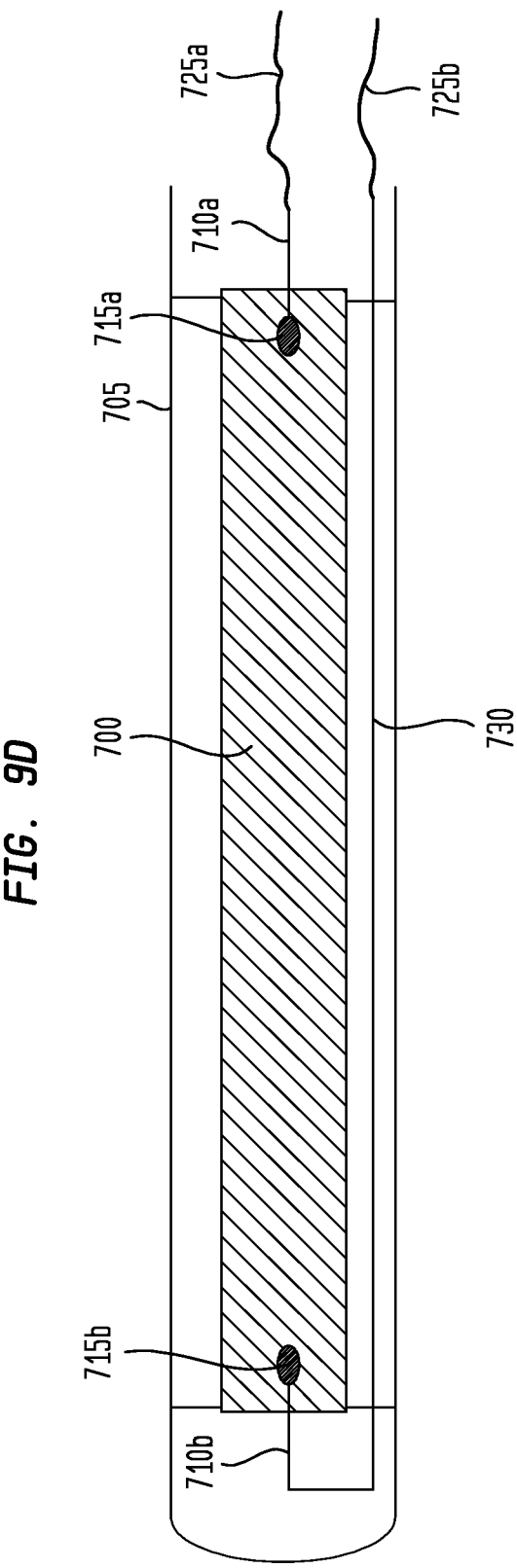
FIG. 9D illustrates another embodiment of a double sided electrical connection lamp utilized in embodiments of a system in accordance with one or more embodiments.

FIG. 9D illustrates an alternate embodiment of a lamp 700 mounted in sleeve 705 in a single end entry configuration. In this embodiment, electrical contact is made via electrical conductor 725a to electrical contact 710a on a first side of the lamp 700. Electrical contact is made via electrical conductor 725b to electrical contact 710b by a conductor 730, for example, a wire or rail disposed external to the body of the lamp 700 within the sleeve 705. The embodiment of FIG. 9D may be appropriate for medium pressure UV lamps operating at temperatures of about 700° C. to about 900° C. where an internal conductor as illustrated in FIG. 9A might not provide a desired level of reliability.

FIG. 3 exemplarily shows a cross-sectional view of a reactor vessel 300 that can be used in system 100 or system 200 or both. Reactor vessel 300 typically comprises inlet 310, outlet 320, and baffle 315 which divides reactor vessel 300 into upper chamber 325 and lower chamber 330. Reactor vessel 300 can also comprise manifold 305 which can be configured to distribute water introduced through inlet 310 throughout the vessel. In certain embodiments, manifold 305 can be configured to evenly distribute water throughout the vessel. For example, manifold 305 can be configured to evenly distribute water throughout the vessel such that the reactor operates as a plug flow reactor.

In some embodiments, the reactor vessel may comprise more than one baffle 315 to divide the reactor vessel into more than two chambers. Baffle 315 can be used to provide mixing or turbulence to the reactor. In certain embodiments, as shown in FIG. 3, reactor inlet 310 is in fluid communication with lower chamber 330 and reactor outlet 320 is in fluid communication with upper chamber 325.

In some embodiments, at least three reactor chambers, each having at least one ultraviolet (UV) lamp disposed to irradiate the water in the respective chambers with light of about or ranging from about 185 nm to about 254 nm, 220 nm, and/or 254 nm at a desired or at various power levels, are serially arranged in reactor 120.

The reactor vessel can also comprise a plurality of ultraviolet lamps positioned within tubes, for example tubes 335a-c and 340a-c. In one embodiment, as shown in FIG. 3, reactor vessel 300 comprises a first set of parallel tubes, tubes 335a-c and a second set of parallel tubes (not shown). Each set of parallel tubes of the first set is approximately orthogonal to the second set to form first array 345. Tubes 335a-c and the second set of parallel tubes are at approximately the same elevation in reactor vessel 300, relative to one another.

Further, the reactor vessel can comprise a third set of parallel tubes and a fourth set of parallel tubes. Each set of parallel tubes of the first set is approximately orthogonal to the second set to form, for example, second array 350. As exemplarily illustrated, tubes 340a-c and the second set of parallel tubes are at approximately the same elevation in reactor vessel 300, relative to one another. As shown in FIG. 3, first array 345 can be positioned at a predetermined distance from second array 350. Vessel 300 can additionally comprise third array 355 and fourth array 360, each optionally having similar configurations as first array 340 and second array 345.

In another embodiment, a first tube 335b can be arranged orthogonal to a second tube 340b to form a first array. Additionally, a set of tubes, tube 365a and tube 365b can be arranged orthogonal to another set of tubes, tube 370a and tube 370b to form a second array. The position of the lamps of the second array are shown in FIG. 4A, including lamps 414, 420, 422, and 424. The positions of the lamps in the first array and the second array are shown in FIG. 4B, including lamps 426 and 428 of the first array and lamps 414, 420, 422, and 424 of the second array.

The lamps can generate a pattern, depending on various properties of the lamp, including the dimensions, intensity, and power delivered to the lamp. The light pattern generated by the lamp is the general volume of space to which that the lamp emits light. In certain embodiments the light pattern or illumination volume is defined as the area or volume of space that the lamp can irradiate or otherwise provide actinic radiation to and allow for division or conversion of the precursor compound into the one or more free radical species.

Figure 4B:
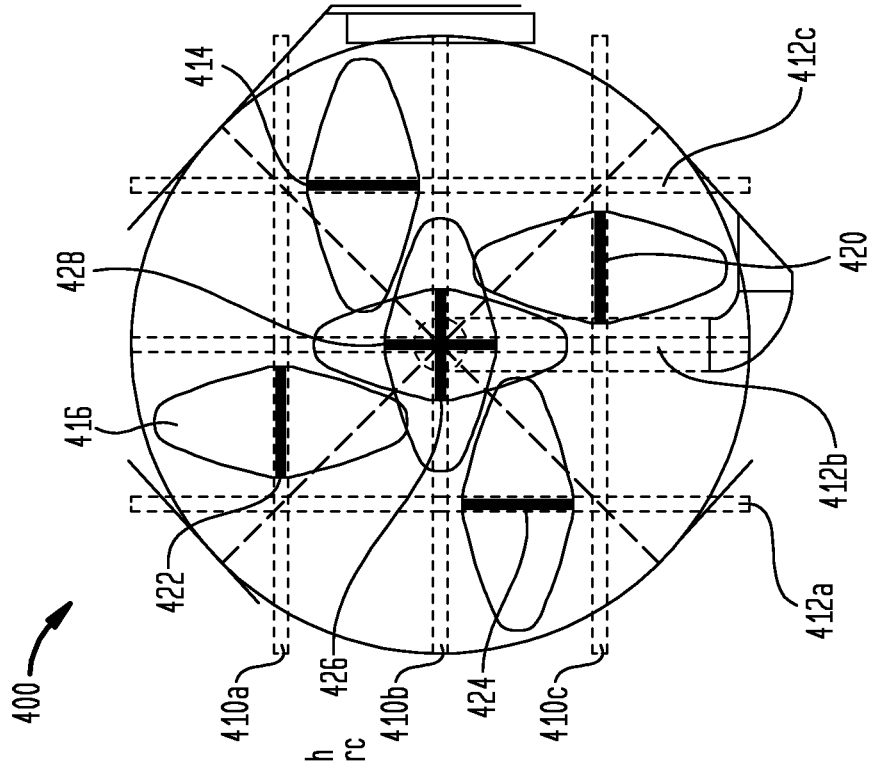
FIG. 4B is a schematic drawing illustrating a vessel in accordance with one or more embodiments.
Figure 4A:
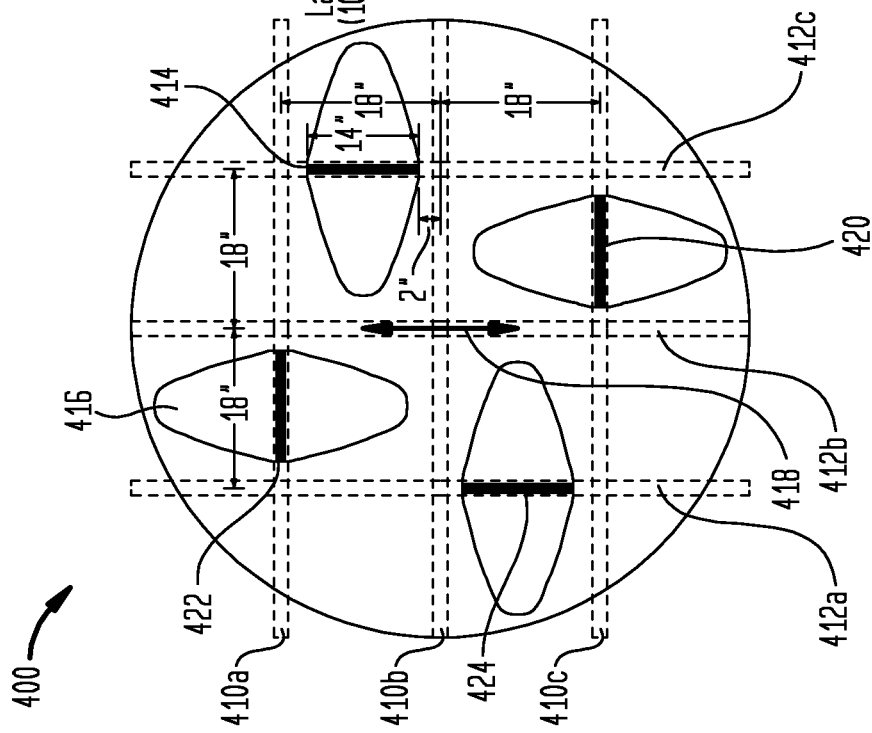
FIG. 4A is a schematic drawing illustrating a vessel in accordance with one or more embodiments.

As shown in FIGS. 4A and 4B, which shows exemplarily cross-sectional views of reactor 400 in which a first set of tubes 410a-c are arranged parallel to one another, and a second set of tubes 412a-c are arranged parallel to one another. As shown, first set of tubes 410a-c is arranged orthogonal relative to second set of tubes 412a-c. Lamps, such as lamps 414, are dispersed within tubes 410a-c and 412a-c, and when illuminated, can generate light pattern 416.

One or more ultraviolet lamps, or a set of lamps, can be characterized as projecting actinic radiation parallel an illumination vector. The illumination vector can be defined as a direction in which one or more lamps emits actinic radiation. In an exemplarily embodiment, as shown in FIG. 4A, a first set of lamps, including lamp 420 and 422, is disposed to project actinic radiation parallel to illumination vector 418.

A first set of ultraviolet lamps each of which is disposed to project actinic radiation parallel a first illumination vector can be energized. A second set of ultraviolet lamps each of which is disposed to project actinic radiation parallel a second illumination vector can also be energized. At least one of the direction of the illumination and the intensity of at least one of the first set of ultraviolet lamps and second set of ultraviolet lamps can be adjusted. Each set of ultraviolet lamps can comprise one or more ultraviolet lamps.

The number of lamps utilized or energized and the configuration of the lamps in use can be selected based on the particular operating conditions or requirements of the system. For example, the number of lamps utilized for a particular process can be selected and controlled based on characteristics or measured or calculated parameters of the system. For example measured parameters of the inlet water or treated water can include any one or more of TOC concentration, temperature, and flow rate. The number of energized lamps can also be selected and controlled based on the concentration or amount of persulfate added to the system. For example, 12 lamps in a particular configuration can be used if the flow rate of the water to be treated is at or below a certain threshold value, for example a nominal or design flow rate, such as 1300 gpm, while more lamps can be used if the flow rate of the water to be treated rises above the threshold value. For example, if the flow rate increases from 1300 gpm to a selected higher threshold value, additional lamps can be energized. For example, 24 lamps may be used if the flow rate of the water to be treated reaches 1900 gpm. Thus the flow rate of the water can be partially determinative of which lamps and/or the number of energized lamps in each reactor.

In certain embodiments, the ultraviolet lamps can be operated at one or more illumination intensity levels. For example, one or more lamps can be used that can be adjusted to operate at a plurality of illumination modes, such as at any of dim, rated, and boost mode, for example, a low, medium, or high mode. The illumination intensity of one or more lamps can be adjusted and controlled based on characteristics or measured or calculated parameters of the system, such as measured parameters of the inlet water or treated water, including TOC concentration, temperature, and flow rate. The illumination intensity of one or more lamps can also be adjusted and controlled based on the concentration or amount of persulfate added to the system. For example, the one or more lamps can be used in a dim mode up to a predetermined threshold value of a measured parameter of the system, such as a first TOC concentration. The one or more lamps can be adjusted to rated mode if the measured or calculated TOC concentration reaches or is above a second TOC concentration, which may be above the threshold value. The one or more lamps can further be adjusted to a boost mode if the measured or calculated TOC concentration reaches or is above a second threshold value.

The lamps and the illumination intensity thereof can be controlled together or separately, using the same or different measured parameters and values as thresholds for adjustment.

In some embodiments, the reactor can operate in a first mode which is indicative of a first lamp configuration and a first lamp intensity. The reactor can operate at the first mode for a particular range or up to a selected or desired value of one or more parameters of the system. For example, the reactor can operate at the first mode for a particular range or up to a selected or desired value, such as a first threshold value, of one or more of the TOC concentration, amount and/or rate of addition of persulfate, and flowrate of the inlet water or the flowrate of the water going through the reactor. At or above the selected or desired value of one or more of the parameters, or a first threshold value, the reactor can operate in a second mode which is indicative of at least one of a second lamp configuration and a second lamp intensity. The reactor can operate in the second mode for a particular range or up to a selected or desired value, such as a second threshold value, of one or more parameter of the system. At or above the second threshold value, the reactor can operate in a third mode which is indicative of at least one or a third lamp configuration and a third lamp intensity.

The system can also be designed such that the reactor can be operated to allow adjustment from the third mode to the second mode, or the second mode to the first mode based on one or more selected or desired threshold values. The system can be operated such that one or more threshold levels are selected or inputed into the system, and the system can be operated in one or more operating modes.

In some particular embodiments, for example, the first mode may be indicative of the system operating at less than 30% of the designed flow rate capacity of the system, or less than 30% of the TOC concentration of the target TOC concentration of the inlet water, or less than 30% of the maximum amount or rate of addition of persulfate that can be added to the reactor. The second mode may be indicative of the system operating at 30% to 100% of the designed flow rate capacity of the system, or 30% to 100% of the TOC concentration of the target TOC concentration of the inlet water, or 30% to 100% of the maximum amount or rate of addition of persulfate that can be added to the reactor. The third mode may be indicative of the system operating at greater than 100% of the designed flow rate capacity of the system, or greater than 100% of the TOC concentration of the target TOC concentration of the inlet water, or greater than 100% of the maximum amount or rate of addition of persulfate that can be added to the reactor.

TOC measurements can be made at one or more points along the flow path of the water through the system, for example, system 100 or system 200. TOC measurements can be performed prior to addition of a precursor compound to the actinic radiation reactor or to the water stream. In certain embodiments TOC measurements are made on a water sample that has been processed through a mixed bed ion exchange column so as to remove ionic compounds from the water sample that may interfere with the TOC measurement. The mixed bed ion exchange column can comprise anionic and cationic resins that allow the transfer of ionic species from the water onto the resin, thereby removing at least a portion of these species from the water. By removing the ionic species from the water, the TOC measurement can be performed more accurately. In particular examples, the mixed bed ion exchange column may be located downstream from a reverse osmosis unit, and upstream of the actinic radiation reactor. The mixed bed ion exchange column may utilize USF™ NANO resin from Evoqua Water Technologies LLC., Warrendale, PA.

TOC measurements can also be made downstream of primary actinic radiation reactor 218 or downstream of secondary actinic radiation reactor 221.

In some aspects, measurement of a compound in the water to be treated or being treated can be performed. This can involve measuring a characteristic of the water. The measurement can also involve converting a first species in the water to a target species, or changing a characteristic of the water, and re-measuring the characteristic of the water. In certain examples, the target species can be sulfate ions. The measurement of the compound can be performed down to levels, for example, of less than 1 ppm. In some examples, the measurement of the compound can be performed down to levels of, for example, less than 100 ppb, 1 ppb, or 0.5 ppb.

In certain embodiments, the measurement of a compound in the water can involve measuring a first conductivity of the water or liquid stream, irradiating at least a portion of the water or liquid stream, measuring a second conductivity of the water or liquid stream after irradiating, and calculating a concentration of the compound based at least in part on the first conductivity measurement and the second conductivity measurement. The compound that is measured can be persulfate. Irradiating the water or liquid stream can comprise converting at least a portion of the compound comprising persulfate into sulfate ions. The compound that is measured can also be a reducing agent such as sulfur dioxide. Irradiating the water or liquid stream can comprise converting at least a portion of the compound comprising sulfur dioxide to sulfate ions. The measurement of the compound in the water can be performed on the water stream being treated, for example, in system 100 or system 200, or can be performed on a side stream of the water being treated in system 100 or system 200.

As shown in FIG. 2, using sensor 207, a measurement of the amount of a compound in the water or liquid stream can be provided by, for example, concentration or conductivity measurements. In some embodiments, a first conductivity of the water stream output of vessel 220 can be measured. This water stream can be irradiated by ultraviolet light, and a second conductivity of the water stream can be measured. By comparing the first conductivity measurement to the second conductivity measurement, a concentration or amount of persulfate in the water stream can be determined. In some embodiments, a catalyst may be used instead of utilizing ultraviolet light.

Similarly, using sensor 208, a measurement of the amount of reducing agent in the water or liquid stream can be provided. A first conductivity of the water stream downstream from point of addition 230 of reducing agent from the source of reducing agent 224 can be measured using sensor 208. This water stream can be irradiated by ultraviolet light, and then a second conductivity of the water stream can be measured. By comparing the first conductivity measurement to the second conductivity measurement, a concentration or amount of reducing agent in the water stream can be determined. In some embodiments, a catalyst may be used instead of utilizing ultraviolet light.

Figure 5:
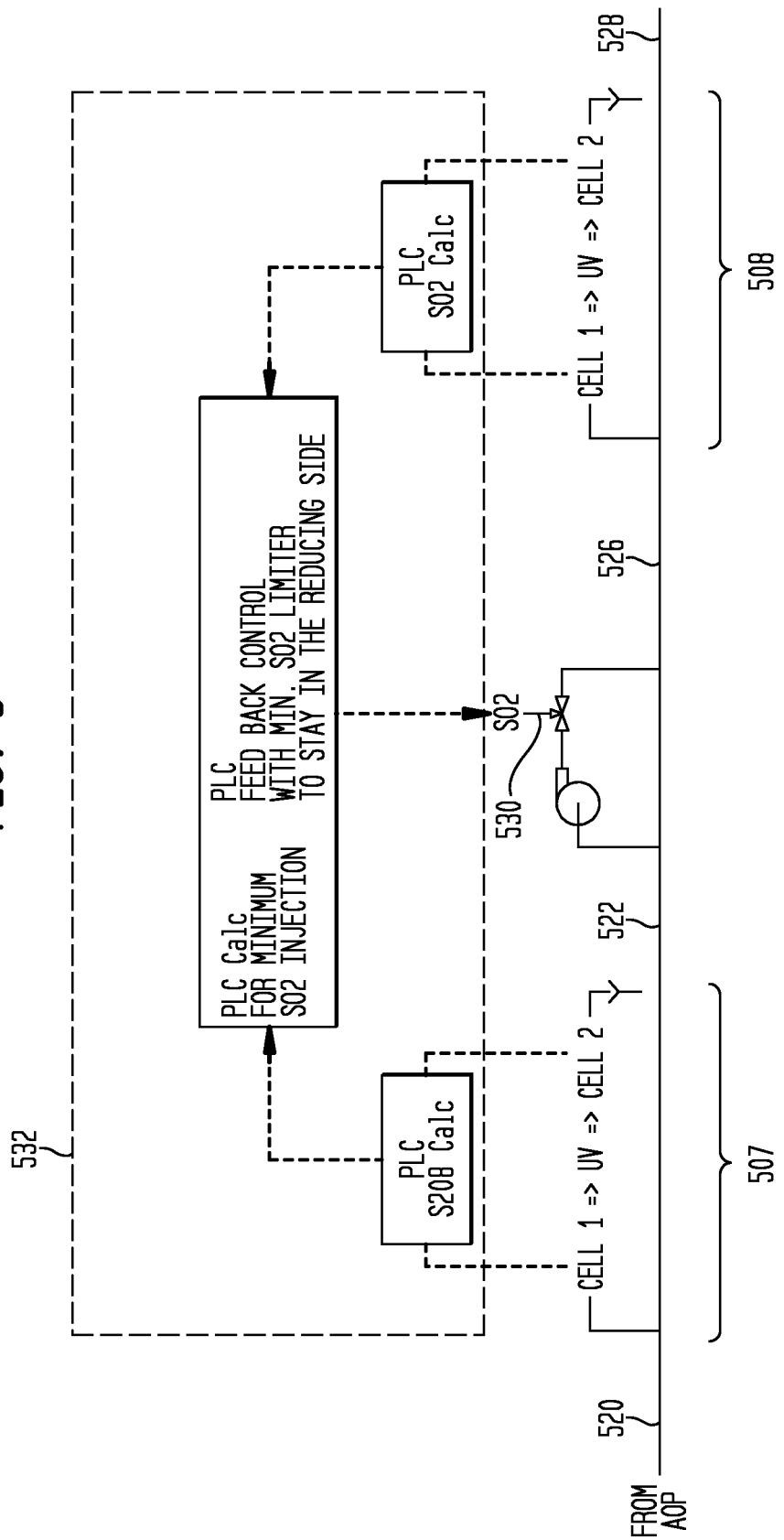
FIG. 5 is a schematic drawing illustrating a sensor and controller system in accordance with one or more embodiments.

One embodiment utilizing sensor 207 and sensor 208 is shown in FIG. 5. A water stream 520 which may be an output from a primary actinic radiation reactor or a secondary radiation reactor may be measured with sensor 507. Sensor 507 can measure a first conductivity of water stream 520. This water stream can then be irradiated by ultraviolet light, and a second conductivity of water stream 520 can be measured. Using controller 532, a concentration or amount of persulfate in the water stream can be determined by comparing the first conductivity measurement to the second conductivity measurement.

Similarly, using sensor 508, a measurement of the amount of reducing agent, such as sulfur dioxide, in water or liquid stream 526 can be provided. A first conductivity of water stream 526, which is downstream from point of addition 530 of reducing agent can be measured using sensor 508. The sensor can irradiate water stream 526 with ultraviolet light, and then a second conductivity of water stream 526 can be measured. Using controller 532, a concentration or amount of reducing agent in the water stream can be determined by comparing the first conductivity measurement to the second conductivity measurement.

At least one of the calculated concentration or amount of persulfate and the calculated concentration or amount of reducing agent in water stream 520 and water stream 526 can be utilized by controller 532 to control the rate or amount of reducing agent added to water stream 522. In certain embodiments, the rate or amount of reducing agent is controlled to provide a minimum amount of reducing agent based on the calculated concentration of persulfate measured using sensor 507. The rate or amount of reducing agent can also be controlled to provide a minimum amount of reducing agent based on the calculated concentration of reducing agent measured using sensor 508.

In certain embodiments, the persulfate ($S_2O_8$) concentration, for example in stream 222 or 522, can be calculated based on the following formula:

$$S_2O_8(ppb) = [\text{conductivity cell } 2(\mu S) - \text{conductivity cell } 1(\mu S)] \times \gamma,$$

wherein $\gamma$ is a constant determined based on, for example, the conductivity of sulfate and the conductivity of persulfate.

Although FIG. 5 is illustrated with each of sensor 507 and sensor 508 comprising two conductivity cells, it can be envisioned that each of sensor 507 and sensor 508 can comprise one conductivity cell in which a first conductivity of a water sample is measured, irradiation of the water sample occurs, and a second conductivity of the water sample is measured. The above equation can be used to determine the persulfate concentration, wherein 'conductivity cell 2' represents the second measured conductivity of the water, and 'conductivity cell 1' represents the first measured conductivity of the water.

In certain embodiments, it is desired to reduce or neutralize residual persulfate in the irradiated water that exits the actinic radiation reactor to a target level. This may be achieved by including additional ultraviolet lamps or actinic radiation lamps downstream from the primary actinic radiation reactor, which can help reduce the residual persulfate and reduce TOC. For example, FIG. 2 includes secondary actinic radiation reactor 220 which can be added to help reduce the residual persulfate and reduce the TOC in the water.

Techniques such as utilizing catalysts or reducing agents can be used to reduce or neutralize the residual persulfate in the water stream. Reducing agents may include bisulfites and sulfur dioxide. The reducing agent can be added to the water stream based on the persulfate and reducing agent measurements, or other characteristics or properties of the system. The rate of addition can be adjusted during the process as the needs of the system changes.

Systems 100 and 200 can further comprise one or more control systems or controllers 105 and 232. Control systems 105 and 232 are typically connected to one or more sensors or input devices configured and disposed to provide an indication or representation of at least one property, characteristic, state or condition of at least one of a process stream, a component, or a subsystem of treatment systems 100 and 200. For example, control system 105 can be operatively coupled to receive input signals from any one or more of source 110 and sensors 106, 107, and 108. Control system 232 can be operatively coupled to receive input signals from any one or more of source 210 and sensors 206, 207, 208, and 209. The input signals can be representative of any intensive property or any extensive property of the water from source 110, or water stream in the system. For example, input signals can be representative of any intensive property or any extensive property of the treated ultrapure water from ion exchange column 140L, and ion exchange column 140P of FIG. 1. The input signals can also be representative of any intensive property or any extensive property of the treated ultrapure water from reverse osmosis unit 212, secondary actinic radiation reactor 220, or after point of addition of reducing agent 230. For example, one or more input signals from source 110 or source 210 can provide an indication of the resistivity or conductivity, the flow rate, the TOC value, the temperature, the pressure, the concentration of metals, the level or amount of bacteria, the dissolved oxygen content, and/or the dissolved nitrogen content of the inlet or make-up water. Input devices or sensors 106, 107 and 108, and 206, 207, 208, and 209 may likewise provide any one or more such representations of the at least partially treated water through system 100 or system 200. In particular, any one of the sensors can provide an indication of the temperature, conductivity, or concentration of a particular compound or species in the at least partially treated water or ultrapure water. Although only sensors 106, 107, and 108 and 206, 207, 208, and 209 are particularly depicted, additional sensors may be utilized including, for example, one or more temperature, conductivity or resistivity sensors in systems 100 and 200.

Control systems 105 and 232 can be configured to receive any one or more input signals and generate one or more drive, output, and control signals to any one or more unit operations or subsystems of treatment systems 100 and 200. As illustrated, control systems 105 and 232 can, for example, receive an indication of a flow rate, a TOC level, or both, of water from source 110 and/or 210, or from another position within the system. Control systems 105 and 232 can then generate and transmit a drive signal to source 122 or source 216 of precursor compound to, if necessary, adjust the rate of addition of the precursor compound introduced into the water stream entering reactor 120 or reactor 218. In one embodiment, control system 232 can, for example, receive an indication of a concentration of a particular compound or species in the water from sensor 207 and sensor 208. Control system 232 can then generate and transmit a drive signal to source 224 of reducing agent to, if necessary, adjust the rate of addition of the reducing agent introduced into the water stream at point of addition 230. The drive signal is typically based on the one or more input signals and a target or predetermined value or set-point. For example, if the input signal that provides a representation of the TOC value of the inlet water from source 110 or source 210 is above the target TOC value or a range of acceptable TOC value, i.e., a tolerance range, then the drive signal can be generated to increase an amount or a rate of addition of the precursor compound from source 122 or source 216. The particular target values are typically field-selected and may vary from installation to installation and be dependent on downstream, point of use requirements. This configuration inventively avoids providing water having undesirable characteristics by proactively addressing removal of contaminants and also avoids compensating for the system's residence or lag response time, which can be a result of water flowing through the system and/or the time required for analysis.

In some embodiments, control systems 105 and 232 can, for example, receive an indication of a flow rate, a TOC concentration or level, and/or a persulfate amount or rate of addition, and generate and transmit a drive signal to reactor 120 or reactor 218 or 220, or more specifically to the lamps of the reactor to adjust or modify at least one of the one or more lamps in operation and the intensity of the lamps. The drive signal can be based on the one or more input signals and a target or predetermined value or set-point, or threshold value. For example, if the input signal that provides a representation of the TOC value of the inlet water from source 110 or source 210 is above the target TOC value or threshold value, or a range of acceptable TOC value, i.e., a tolerance range, then the drive signal can be generated to adjust the operating mode of the reactor by adjusting at least one of the lamp configuration and the lamp intensity.

Control systems 105 and 232 may further generate and transmit additional control signals to, for example, energize or adjust an intensity or power of output radiation emitted by at least one radiation source in reactor 120, 218, or 220. Thus, depending on the amount or rate of addition of the precursor compound, or on the level of TOC in the water stream entering the reactors, the control signal may be increased or decreased appropriately, incrementally or proportionally. This feature serves to prolong service life of the one or more radiation sources and reduce energy consumption.

Control systems 105 and 232 may also be configured in feedback arrangement and generate and transmit one or more control signals to any one or both of the precursor compound source 122 and 214, and reactors 120, 218, and 220, and reducing agent source 224. For example, the TOC value or the resistivity, or both, of the ultrapure product water in distribution system 103, or from the sensors 107 or 108, may be utilized to generate control signals to any of source 122 and reactor 120.

During periods of high initial TOC fluctuations, the feedforward control can be utilized to compensate for instrument delay. This preemptive approach injects the precursor compound, typically at a surplus relative to the amount of contaminants. During periods of stable TOC levels, the feedback approach may be utilized with or without the feedforward control.

Control system 105 may further generate and transmit a control signal that adjusts a rate of heat transfer in chiller 130 based on, for example, an input signal from sensors 107 or 108, or both. The control signal may increase or decrease the flow rate and/or the temperature of the cooling water introduced into chiller 130 to provide treated water to distribution system 103 at a desired or predetermined temperature.

Control system 105 may further generate and transmit a control signal that energizes pump 166 or adjust a flow rate of the at least partially treated water flowing therethrough. If the pump utilizes a variable frequency drive, the control signal can be generated to appropriately adjust the pump motor activity level to achieve a target flow rate value. Alternatively, an actuation signal may actuate a valve that regulates a rate of flow of the at least partially treated water from pump 166.

Figure 6:
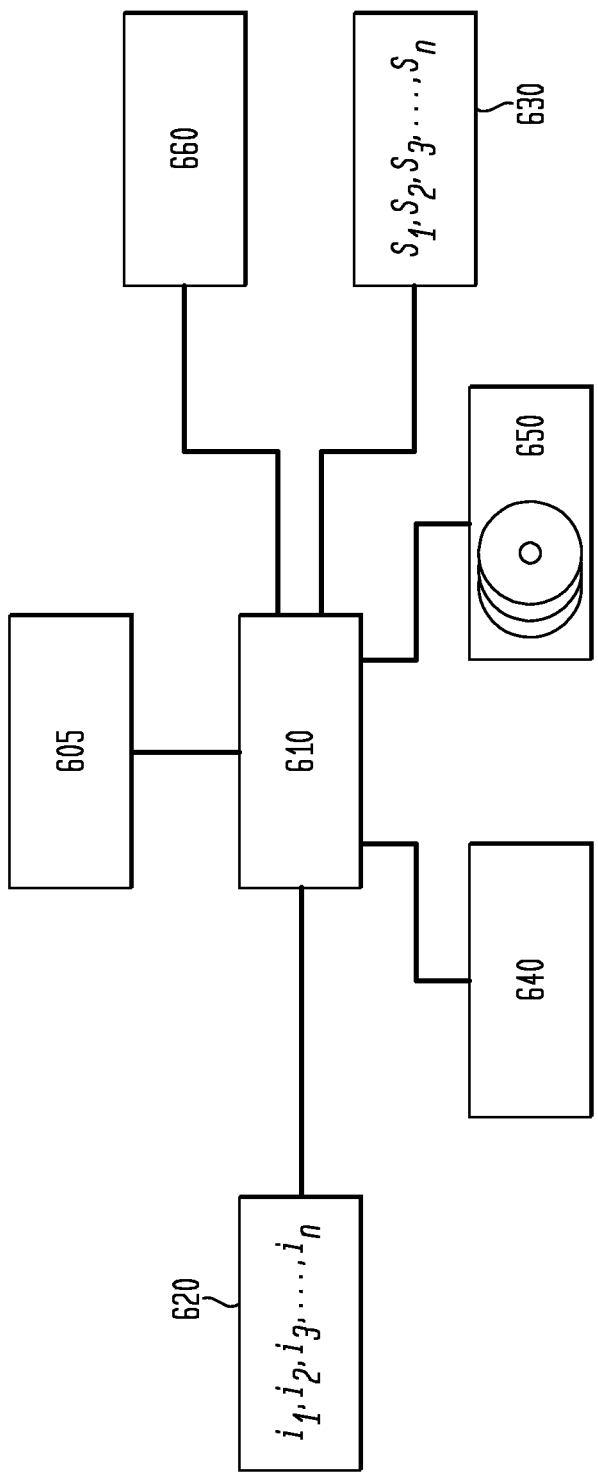
FIG. 6 is a schematic drawing illustrating a processor or control system upon which one or more embodiments may be practiced.

Control systems 105 and 232 may be implemented using one or more processors as schematically represented in FIG. 6. Control system 105 may be, for example, a general-purpose computer such as those based on an Intel PENTIUM®-type processor, a Motorola PowerPC® processor, a Sun UltraSPARC® processor, a Hewlett-Packard PA-RISC® processor, or any other type of processor or combinations thereof. Alternatively, the control system may include specially-programmed, special-purpose hardware, for example, an application-specific integrated circuit (ASIC) or controllers intended for analytical systems.

Control systems 105 and 232 can include one or more processors 605 typically connected to one or more memory devices 650, which can comprise, for example, any one or more of a disk drive memory, a flash memory device, a RAM memory device, or other device for storing data. Memory device 650 is typically used for storing programs and data during operation of the systems 100 and 200 and/or control systems 105 and 232. For example, memory device 650 may be used for storing historical data relating to the parameters over a period of time, as well as operating data. Software, including programming code that implements embodiments, can be stored on a computer readable and/or writeable nonvolatile recording medium, and then typically copied into memory device 650 wherein it can then be executed by processor 605. Such programming code may be written in any of a plurality of programming languages, for example, Java, Visual Basic, C, C #, or C++, Fortran, Pascal, Eiffel, Basic, COBAL, or any of a variety of combinations thereof.

Components of control system 105 and 232 may be coupled by an interconnection mechanism 610, which may include one or more busses, e.g., between components that are integrated within a same device, and/or a network, e.g., between components that reside on separate discrete devices. The interconnection mechanism typically enables communications, e.g., data, instructions, to be exchanged between components of the system.

Control systems 105 and 232 can also include one or more input devices 620 receiving one or more input signals $i_1$, $i_2$, $i_3, \ldots, i_n$, from, for example, a keyboard, mouse, trackball, microphone, touch screen, and one or more output devices 630, generating and transmitting, one or more output, drive or control signals, $s_1, s_2, s_3, \ldots, s_n$, to for example, a printing device, display screen, or speaker. In addition, control systems 105 and 232 may contain one or more interfaces 660 that can connect control systems 105 or 232 to a communication network (not shown) in addition or as an alternative to the network that may be formed by one or more of the components of the system.

According to one or more embodiments, the one or more input devices 620 may include components, such as but not limited to, valves, pumps, and sensors 106, 107, and 108, and 206, 207, 208, and 209 that typically provide a measure, indication, or representation of one or more conditions, parameters, or characteristics of one or more components or process streams of systems 100 and 200. Alternatively, the sensors, the metering valves and/or pumps, or all of these components may be connected to a communication network that is operatively coupled to control systems 105 and 232. For example, sensors 106, 107, and 108 and 206, 207, 208, and 209 may be configured as input devices that are directly connected to control systems 105 and 232, metering valves and/or pumps of subsystems 122 and 124 may be configured as output devices that are connected to control system 105, and any one or more of the above may be coupled to a computer system or an automated system, so as to communicate with control systems 105 and 232 over a communication network. Such a configuration permits one sensor to be located at a significant distance from another sensor or allow any sensor to be located at a significant distance from any subsystem and/or the controller, while still providing data therebetween.

Control systems 105 and 232 can comprise one or more storage media such as a computer-readable and/or writeable nonvolatile recording medium in which signals can be stored that define a program or portions thereof to be executed by, for example, one or more processors 605. The one or more storage media may, for example, be or comprise a disk drive or flash memory. In typical operation, processor 605 can cause data, such as code that implements one or more embodiments, to be read from the one or more storage media into, for example, memory device 640 that allows for faster access to the information by the one or more processors than does the one or more media. Memory device 640 is typically a volatile, random access memory such as a dynamic random access memory (DRAM) or static memory (SRAM) or other suitable devices that facilitates information transfer to and from processor 605.

Although control systems 105 and 232 is shown by way of example as one type of computer system upon which various aspects may be practiced, it should be appreciated that aspects and embodiments disclosed herein are not limited to being implemented in software, or on the computer system as exemplarily shown. Indeed, rather than being implemented on, for example, a general purpose computer system, the control system, or components or subsystems thereof, may be implemented as a dedicated system or as a dedicated programmable logic controller (PLC) or in a distributed control system. Further, it should be appreciated that one or more features or aspects may be implemented in software, hardware or firmware, or any combination thereof. For example, one or more segments of an algorithm executable by processor 605 can be performed in separate computers, each of which can be in communication through one or more networks.

System 100 can further comprise a subsystem 176 for sanitizing and/or removing any residue, particulate or other material retained on the surface of the membranes of filtration apparatus 172 and 174. Subsystem 176 can comprise one or more heat exchangers and pumps that allow temperature cycling of the membranes of apparatus 172 and 174. Temperature cycling can be controlled by control system 105 by alternately providing hot and cool water into any of apparatus 172 and 174 to allow expansion and contraction of components thereof which facilitates removal of any retained materials. Although not illustrated, subsystem 176 may also be connected to any unit operation of system 100 to also facilitate cleaning and hot water sanitization of such unit operations.

Having now described some illustrative embodiments, it should be apparent to those skilled in the art that the foregoing is merely illustrative and not limiting, having been presented by way of example only. Numerous modifications and other embodiments are within the scope of one of ordinary skill in the art and are contemplated as falling within the scope. In particular, although many of the examples presented herein involve specific combinations of method acts or system elements, it should be understood that those acts and those elements may be combined in other ways to accomplish the same objectives.

Those skilled in the art should appreciate that the parameters and configurations described herein are exemplary and that actual parameters and/or configurations will depend on the specific application in which the systems and techniques are used. Those skilled in the art should also recognize or be able to ascertain, using no more than routine experimentation, equivalents to the specific embodiments. It is therefore to be understood that the embodiments described herein are presented by way of example only and that, within the scope of the appended claims and equivalents thereto; the aspects and embodiments disclosed herein may be practiced otherwise than as specifically described.

Moreover, it should also be appreciated that the aspects and embodiments disclosed herein are directed to each feature, system, subsystem, or technique described herein and any combination of two or more features, systems, subsystems, or techniques described herein and any combination of two or more features, systems, subsystems, and/or methods, if such features, systems, subsystems, and techniques are not mutually inconsistent, is considered to be within the scope as embodied in the claims. Further, acts, elements, and features discussed only in connection with one embodiment are not intended to be excluded from a similar role in other embodiments.

As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A system for treating water comprising:
a primary actinic radiation reactor;
a source of a persulfate precursor compound disposed to introduce at least one persulfate precursor compound into the primary actinic radiation reactor;
a total organic carbon (TOC) concentration sensor located upstream of the primary actinic radiation reactor;
a persulfate concentration sensor located downstream of the primary actinic radiation reactor; and
a controller operatively coupled to receive at least one input signal from at least one of the TOC concentration sensor and the persulfate concentration sensor, the controller comprising an electronic ballast circuit including a resonant tank circuit having a power output operatively coupled to a source of actinic radiation having a continuously variable intensity disposed within the primary actinic radiation reactor, the electronic ballast circuit operable to control the continuously variable intensity of the source of actinic radiation over a continuous range of power levels by continuously measuring current supplied to the source of actinic radiation and adjusting a frequency of a drive voltage supplied to the resonant tank circuit responsive to the at least one input signal from the at least one of the TOC concentration sensor and the persulfate concentration sensor, and the measured current supplied to the source of actinic radiation.

2. The system of claim 1, further comprising a reverse osmosis unit located upstream of the primary actinic radiation reactor.

3. The system of claim 1, further comprising a secondary actinic radiation reactor located downstream of the primary actinic radiation reactor.

4. The system of claim 1, further comprising a particulate filter located downstream of the primary actinic radiation reactor.

5. The system of claim 1, further comprising an ultrafiltration apparatus located downstream of the primary actinic radiation reactor.

6. The system of claim 1, further comprising at least one unit operation selected from the group consisting of a heat exchanger, a degasifier, a particulate filter, an ion purification apparatus, and an ion-exchange column.

7. The system of claim 6, wherein the ion-exchange column is located upstream of the TOC concentration sensor.

8. The system of claim 1, further comprising a source of water located upstream of the primary actinic radiation reactor comprising one or more unit operations selected from the group consisting of a reverse osmosis filter, an electrodialysis device, an electrodeionization device, a distillation apparatus, an ion-exchange column, and combinations thereof.

9. The system of claim 8, wherein water from the source of water comprises less than about 25 ppb TOC.

10. The system of claim 1, further comprising a TOC concentration sensor located downstream of the primary actinic radiation reactor.

11. The system of claim 1, wherein the controller is further operable to generate a control signal that regulates a rate at which the persulfate precursor compound is introduced into the primary actinic radiation reactor.

12. The system of claim 1, wherein the primary actinic radiation reactor includes an ultraviolet lamp with a double sided electrical connection.

13. The system of claim 12, wherein the ultraviolet lamp with the double sided electrical connection includes a first electrical connection to a first electrode on a first end of the lamp, a second electrical connection to a second electrode on the first end of the lamp, and a third electrical connection to the second electrode on a second end of the lamp.

14. The system of claim 1, further comprising:
a source of a reducing agent disposed to introduce at least one reducing agent downstream from the primary actinic radiation reactor; and
a reducing agent concentration sensor located downstream of a point of addition of the at least one reducing agent;
wherein the controller is further configured to receive an input signal from the reducing agent concentration sensor and generate a control signal that regulates the continuously variable intensity of the actinic radiation in the primary actinic radiation reactor based at least in part on the input signal from the reducing agent concentration sensor.

15. The system of claim 14, wherein the reducing agent is sulfur dioxide.

16. The system of claim 14, wherein the controller is further operable to generate a control signal that regulates a rate at which the reducing agent is introduced to the system.

17. A method of providing ultrapure water to a semiconductor fabrication unit, comprising:
providing inlet water having a TOC value of less than about 25 ppb;
introducing at least one free radical precursor compound into the water;
converting the at least one free radical precursor compound into at least one free radical scavenging species by exposing the at least one free radical precursor to a UV radiation from a source of UV radiation having a continuously variable UV radiation power output;
controlling the continuously variable UV radiation power output of the source of UV radiation with an electronic ballast circuit including a resonant tank circuit having a power output operatively coupled to the source of UV radiation, the electronic ballast circuit operable to control the continuously variable UV radiation power output of the source of UV radiation over a continuous range of power levels by continuously measuring current supplied to the source of UV radiation and adjusting a frequency of a drive voltage supplied to the resonant tank circuit responsive to at least one input signal based at least partially on a measured TOC value of the inlet water and the measured current supplied to the source of UV radiation;
removing at least a portion of any particulates from the water to produce the ultrapure water; and
delivering at least a portion of the ultrapure water to the semiconductor fabrication unit.

18. The method of claim 17, further comprising regulating a rate of addition of the at least one precursor compound based at least partially on the TOC value of the inlet water.

* * * * *